United States Patent [19]

Phipps et al.

[11] Patent Number: 5,125,894
[45] Date of Patent: Jun. 30, 1992

[54] METHOD AND APPARATUS FOR CONTROLLED ENVIRONMENT ELECTROTRANSPORT

[75] Inventors: Joseph B. Phipps, Plymouth; Lyn C. Moodie, St. Paul, both of Minn.

[73] Assignee: Alza Corporation, Palo Alto, Calif.

[21] Appl. No.: 502,232

[22] Filed: Mar. 30, 1990

[51] Int. Cl.⁵ ............................................. A61N 1/30
[52] U.S. Cl. ..................................... 604/20; 128/783
[58] Field of Search ............... 128/783, 798, 799, 803; 604/20

[56] References Cited

U.S. PATENT DOCUMENTS

| | | |
|---|---|---|
| 2,784,715 | 3/1957 | Kestler . |
| 3,163,166 | 12/1964 | Brant et al. . |
| 3,677,268 | 7/1972 | Reeves . |
| 3,716,054 | 2/1973 | Porter et al. . |
| 3,794,910 | 2/1974 | Ninke et al. . |
| 4,140,122 | 2/1979 | Kuhl et al. . |
| 4,141,359 | 2/1979 | Jacobsen et al. . |
| 4,166,457 | 9/1979 | Jacobsen et al. . |
| 4,211,222 | 7/1980 | Tapper . |
| 4,250,878 | 2/1981 | Jacobsen et al. . |
| 4,301,794 | 11/1981 | Tapper . |
| 4,325,367 | 4/1982 | Tapper . |
| 4,383,529 | 5/1983 | Webster . |
| 4,406,658 | 9/1983 | Lattin et al. . |
| 4,416,274 | 11/1983 | Jacobsen . |
| 4,419,091 | 12/1983 | Behl et al. . |
| 4,474,570 | 10/1984 | Ariura et al. . |
| 4,477,971 | 10/1984 | Jacobsen et al. . |
| 4,557,723 | 12/1985 | Sibalis . |
| 4,602,909 | 7/1986 | Csillik et al. . |
| 4,622,031 | 11/1986 | Sibalis . |
| 4,633,879 | 1/1987 | Ong . |
| 4,639,244 | 1/1987 | Rizk et al. . |
| 4,640,689 | 2/1987 | Sibalis . |
| 4,679,572 | 7/1987 | Baker, Jr. . |
| 4,689,039 | 8/1987 | Masaki . |
| 4,702,732 | 10/1987 | Powers et al. . |
| 4,708,716 | 11/1987 | Sibalis . |

(List continued on next page.)

FOREIGN PATENT DOCUMENTS

0292930 11/1977 European Pat. Off. .
0230153 7/1987 European Pat. Off. .

(List continued on next page.)

OTHER PUBLICATIONS

H. Molitor et al., *Am. J. of Med. Sci.*, 198:778-775 (1939).

(List continued on next page.)

*Primary Examiner*—Francis Jaworski
*Assistant Examiner*—Scott R. Akers
*Attorney, Agent, or Firm*—Merchant, Gould, Smith, Edell, Welter & Schmidt

[57] ABSTRACT

Methods for conducting controlled environment electrotransport are described. The methods generally concern control of the ionic environment of the active electrode reservoir, in an electrotransport system. This control may be utilized, for example, to maintain a constant extraneous ion presence, such as pH. It may also be applied in a preferred manner to maintain selected control over the delivery rate of a target species, in time, in the presence of extraneous ions. Apparatus usable to provide for controlled environment electrotransport are also described. In general the apparatus comprises an electrotransport system including an active electrode reservoir having therein both a primary electrode arrangement and a secondary electrode arrangement, with a control arrangement for selected operation of both. The secondary electrode arrangement, being operated different from the primary electrode arrangement, is selected for operation to selectively enhance or otherwise modify ion presence in the active electrode reservoir, to achieve application of the general methods described. The apparatus may include a sensor means therein, for use as feedback to a control system during operation. Methods and systems involving diffusion type delivery are also described.

10 Claims, 3 Drawing Sheets

U.S. PATENT DOCUMENTS

| | | |
|---|---|---|
| 4,717,581 | 1/1988 | Robblee . |
| 4,722,726 | 2/1988 | Sanderson et al. . |
| 4,725,263 | 2/1988 | McNichols et al. . |
| 4,731,049 | 3/1988 | Parsi . |
| 4,734,090 | 3/1988 | Sibalis . |
| 4,744,787 | 5/1988 | Phipps et al. . |
| 4,747,819 | 5/1988 | Phipps et al. . |
| 4,752,285 | 6/1988 | Petelenz et al. . |
| 4,764,164 | 8/1988 | Sasaki . |
| 4,767,401 | 8/1988 | Seiderman . |
| 4,786,277 | 11/1988 | Powers . |
| 4,808,152 | 2/1989 | Sibalis . |
| 4,817,594 | 4/1989 | Juhasz . |
| 4,822,334 | 4/1989 | Tapper . |
| 4,842,577 | 6/1989 | Konno et al. . |
| 4,865,582 | 9/1989 | Sibalis . |
| 4,883,457 | 11/1989 | Sibalis . |
| 4,886,489 | 12/1989 | Jacobsen et al. . |

FOREIGN PATENT DOCUMENTS

| | | |
|---|---|---|
| 0240189 | 10/1987 | European Pat. Off. . |
| 0240593 | 10/1987 | European Pat. Off. . |
| 0254166 | 1/1988 | European Pat. Off. . |
| 0293893 | 12/1988 | European Pat. Off. . |
| 0299615 | 1/1989 | European Pat. Off. . |
| 0299631 | 1/1989 | European Pat. Off. . |
| 0309093 | 3/1989 | European Pat. Off. . |
| 0318776 | 6/1989 | European Pat. Off. . |
| 0337642 | 10/1989 | European Pat. Off. . |
| 2558525 | 8/1976 | Fed. Rep. of Germany . |
| WO88/00846 | 2/1988 | PCT Int'l Appl. . |
| WO88/08729 | 11/1988 | PCT Int'l Appl. . |
| 0410009 | 5/1934 | United Kingdom . |
| 2030453 | 4/1980 | United Kingdom . |
| 2063072 | 6/1981 | United Kingdom . |

OTHER PUBLICATIONS

W. C. Dautremont-Smith, *Displays*, p. 67 (Apr. 1982).

L. S. Robblee et al., *J. Electrochem. Soc.*, 130:731–733 (1983).

L. Miller et al., *J. Am. Chem. Soc.*, 106: 6861–6863 (1984).

P. G. Pickup et al., *J. Electroanal. Chem.*, 220:83–100 (1987).

J. E. Sanderson et al., *J. Pharm. Sci.*, 76:215–218 (Mar. 1987).

J. B. Phipps et al., *Solid State Ionics*, 28–30:1778–1783 (1988).

Y. W. Chien et al., *J. Controlled Release*, 7:1–24 (1988).

L. Miller et al., *J. Electroanal. Chem.*, 257:173–184 (1988).

L. Miller et al., *J. Electroanal. Chem.*, 261:147–164 (1989).

J. B. Phipps et al., *J. Pharm. Sci.*, 78:365–369 (May 1989).

J. B. Phipps et al., Abstract Presented at Controlled Release Society Meeting (Aug. 1989).

R. B. Padmahabhan et al., *J. of Controlled Release Society*, (Jan. 1990).

METHOD AND APPARATUS FOR CONTROLLED ENVIRONMENT ELECTROTRANSPORT

FIELD OF THE INVENTION

The present invention generally concerns methods and apparatus for electrotransport. More specifically, methods of the present invention concern conduction of electrotransport with selected control of active electrode reservoir environment, to advantage. The present invention also specifically concerns apparatus for providing controlled active electrode environment electrotransport. Two methods of electrotransport to which the invention has particular preferred application are iontophoresis and electro-osmosis. Some of the principles described herein may be applied to passive delivery processes (not involving electrotransport) to advantage.

BACKGROUND OF THE INVENTION

The present invention concerns preferred methods and apparatus for transdermal delivery or transport of therapeutic agents, typically through electrotransport. Herein the term "electrotransport" is used to refer to methods and apparatus for transdermal delivery of therapeutic agents, whether charged or uncharged, by means of an applied electromotive force to electrolyte-containing reservoir. The particular therapeutic agent being delivered may be charged or uncharged, depending upon the particular method chosen. When the therapeutic species being delivered is charged, the process is referred to as iontophoresis. When the therapeutic species delivered is uncharged, it may be considered delivered by means of electro-osmosis techniques or other electrokinetic phenomenon such as electrohydrokinesis, electro-convection or electrically-induced osmosis. In general, these latter electrokinetic delivery processes of uncharged species into a tissue result from the migration of solvent, in which the uncharged species is dissolved, as a result of the application of electromotive force to the electrolyte reservoir. Of course during the process, some transport of charged species will take place as well.

In general, iontophoresis is an introduction, by means of electric current, of ions of soluble salts into the tissues of the body. More specifically, iontophoresis is a process and technique which involves the transfer of ionic (charged) species into a tissue (for example through the skin of a patient) by the passage of a electric current through an electrolyte solution containing ionic molecules to be delivered (or precursors for those ions), upon application of an appropriate electrode polarity. That is, ions are transferred into the tissue, from an electrolyte reservoir, by application of electromotive force to the electrolyte reservoir.

Much of the discussion herein will focus on techniques for iontophoresis, and apparatus therefor. However, the methods and apparatus will be understood to be applicable to electrotransport generally, including electrokinetic phenomena involving transport of an uncharged therapeutic species. A reason for this, is that such phenomena generally involve the transport of some charged species, which is accompanied by the desired movement of an uncharged therapeutic species.

Assume, for example, that the patient to receive the therapeutic ion treatment is a human and the medication is to be transferred through the skin. Through iontophoresis, either positively charged drugs (medication) or negatively charged drugs (medication) can be readily transported through the skin and into the patient. This is done by setting up an appropriate potential between two electrode systems (anode and cathode) in electrical contact with the skin. If a positively charged drug is to be delivered through the skin, an appropriate electromotive force can be generated by orienting the positively charged drug species at a reservoir associated with the anode. Similarly, if the ion to be transferred across the skin is negatively charged, appropriate electromotive force can be generated by positioning the drug in a reservoir at the cathode. Of course, a single system can be utilized to transfer both positively charged and negatively charged drugs into a patient at a given time; and, more than one cathodic drug and/or more than one anodic drug may be delivered from a single system during a selected operation. For general discussions of iontophoresis see: Phipps, J. B. et al; "Transport of Ionic Species Through Skin"; Solid State Ionics; Vol. 28-30, p. 1778-1783 (1988); Phipps, J. B., et al; "Iontophoretic Delivery of Model Inorganic and Drug Ions"; J. Pharm. Sciences; Vol. 78, No. 5, p. 365-369 (May 1989); and, Chien, Y. W. et al; "Iontophoretic Delivery of Drugs: Fundamentals, Developments and Biomedical Applications"; J. Controlled Release, Vol. 7, p. 1-24 (1988). The disclosures of these three references are incorporated herein by reference.

Electrotransport processes, including iontophoresis, have found a wide variety of therapeutic applications. Such applications have sometimes involved the delivery of ionic drugs, i.e., charged organic medications or therapeutic metal ions. Applications have involved both treatments of conditions and also diagnostics. For example, iontophoresis techniques have been utilized to deliver pilocarpine, a substance utilized in the diagnosis of cystic fibrosis. It has also been utilized to deliver hyaluronidase, for treatment of scleroderma and lymphedema. It has further been utilized for allergy testing, delivery of metallic ions for treatment of fungal infections, venereal diseases, ulcers, bursitis, and myopathies; delivery of vasodilators; and, for delivery of anesthetics and steroids. See for example Chien, Y. W., et al., supra.

A wide variety of iontophoresis devices are presently known. See for example: Phipps et al., U.S. Pat. No. 4,744,788; Phipps et al., U.S. Pat. No. 4,747,819; Tapper et al., European Patent Application Publication No. 0318776; Jacobsen et al., European Patent Application Publication No. 0299631; Petelenz et al., U.S. Pat. No. 4,752,285; Sanderson et al., U.S. Pat. No. 4,722,726; and Parsi, E. J., U.S. Pat. No. 4,731,049. The disclosures of these seven references are incorporated herein by references.

In typical, conventional, electrotransport devices, for example iontophoresis devices, two electrodes are generally used. Both electrodes are disposed so as to be an intimate electrical contact with some portion (typically skin) of the subject (human or animal) typically by means of two remote electrolyte-containing reservoirs, between which current passes as it moves between the skin and the electrodes. One electrode, generally referred to herein as the "active" electrode, is the electrode from which the substance (medicament, drug precursor or drug) is delivered or driven into the body by application of the electromotive force. The other electrode, typically referred to as an "indifferent" or "ground" electrode, serves to close the electrical circuit through the body. In some instances both electrodes may be "active", i.e. drugs may be delivered from both.

In such cases each electrode will serve as the "companion", "indifferent", "remote" or "ground" electrode, to the other. That is, classification of an electrode as "active" or "indifferent" is done by reference to a particular material being delivered. Herein the term electrode, or variants thereof, when used in this context refers to an electrically conductive member, through which a current passes during operation.

If the electrotransport method is iontophoresis, generally the active electrode includes the therapeutic species as a charged ion, or a precursor for the charged ion, and the transport occurs through application of the electromotive force to the charged therapeutic species. If other electrotransport phenomenon are involved, the therapeutic species will be delivered in an uncharged form, transfer being motivated, however, by electromotive force. For example, the applied current may induce movement of a non-therapeutic species, which carries with it water into the subject. The water may have dissolved therein the therapeutic species. Thus, electrotransport of the non-therapeutic charged species induces movement of the therapeutic but non-charged species.

In conjunction with the patient's skin in electrical communication with the electrodes, the circuit is completed by connection of the two electrodes to a source of electrical energy as a direct current; for example, a battery or a source of appropriately modified alternating current. As an example, if the ionic substance to be driven to the body is positively charged, then the positive electrode (the anode) will be the active electrode and the negative electrode (the cathode) will serve to complete the circuit. If the ionic substance to be delivered is negatively charged, then the negative electrode (cathode) will be the active electrode and the positive electrode (anode) will be the indifferent electrode.

Again, electrotransport devices generally require a reservoir as a source of the species (or a precursor of such species) which is to be moved or introduced into the body. If the device is an iontophoresis device, in general the reservoir is a pool of electrolyte solution, for example an aqueous electrolyte solution or a hydrophilic, electrolyte-containing, gel or gel matrix or absorbent material. Such drug reservoirs, when electrically connected to the anode or the cathode of an iontophoresis device, provide a source of one or more ionic species for electrotransport.

Herein, for electrotransport processes, the reservoir associated with the active electrode will be referred to as the "active electrode reservoir." It is this reservoir which includes the "target species" or "therapeutic species," for transport; if as a charged species more specifically for electrotransport. The reservoir associated with the other electrode will be referred to herein as the "inactive" or "indifferent" electrode reservoir.

Systems of particular interest to the present application are "closed" reservoir systems. These are systems in which the active electrode reservoir is not replenished during operation, by a remote source of electrolyte solution. Thus, changes in reservoir content during electrotransport will generally be those due to the electrode operation (in addition to diffusion).

During many conventional electrotransport processes, ionic species, in addition to the charged drug species or therapeutic species to be transported, are generated or provided at the active electrode. For example, if the active electrode is the anode, and it is formed from a metal oxidizable under the operating potentials of the system, it will serve as a source of metal cations corresponding to the material from which the electrode is made. Also, again as an example, hydronium ion content (i.e. pH) may change during operation of certain electrodes (e.g., platinum, glass carbon or stainless steel electrodes).

During iontophoresis, since the therapeutic agent(s) is charged, it must compete with other similarly charged ions in the reservoir, for electrotransport through the skin and into the patient under the electromotive force of the applied potential. For example, if the active electrode is the anode, and the drug is to be delivered in a positively charged form, the positively charged drug must compete for transport with all other positively charged species in the reservoir or formed during the operation of the electrode and allowed to remain in solution in the reservoir. It follows, then, that for a constant current, efficiency of transport of the desired drug species across the skin membrane is reduced, if the operation of the active electrode involves generation of (or motivation of) competing species in the active electrode reservoir. This observation will hold whether the active electrode is the anode or the cathode.

Herein species in the active electrode reservoir similarly charged to the selected species for electrotransport (or transport) by iontophoresis (i.e. similarly charged to the target or therapeutic ions $T_i$) will be referred to as "extraneous" ions ($X_i$). For example, if the drug species to be selectively transferred is a positively charged species, all other cations in the active electrode reservoir will be referred to as "extraneous" ions or "extraneous cations". Alternatively, if the drug or treatment species to be transferred across the skin is negatively charged, all other anionic species in the active electrode reservoir will be referred to as "extraneous ions" or "extraneous anions". In general, the presence of extraneous ions reduces the efficiency of transport of a selected (i.e. target or therapeutic) ion, for a given iontophoresis system.

Alternatively, extraneous ions may be defined as those ions which will be transported from an active electrode reservoir, under applied potential, other than therapeutic species (if the therapeutic species is charged). That is, if the therapeutic species is uncharged, extraneous ions will be those ions which are delivered from the reservoir under the applied potential, during operation of the system.

Herein the term "target species", or "therapeutic species" and variants thereof refer in general to the agent to be selectively transported into subject for example by application of potential, whether that species is charged or not. Herein the terms "target ion", "therapeutic ion" and variants thereof refer to the particular ion species to be delivered by the iontophoresis process for therapy. In many instances the target ion will be a drug ion, or a selected metal ion. These species need not be the precise therapeutic agent(s) which operate in the body of the subject. They could, for example, be precursors to such agents. The terms are also intended to include within their scope ions delivered for purposes other than to treat some condition, for example to facilitate diagnoses. Thus, herein the term "therapy" and variants thereof is meant to include treatments of conditions, diagnostic procedures and other processes of medicine wherein an agent is delivered to a subject.

Methods have been developed to generate relatively extraneous ion free, or reduced extraneous ion concentration, systems. See for example the methods and apparatus described in U.S. Pat. Nos. 4,747,819 and 4,744,787 to Phipps et al., incorporated herein by reference and assigned to Medtronic, Inc., Minneapolis, Minn., the assignee of the instant invention. A basic principle of these methods is that the active electrode and/or components of the active electrode reservoir are selected such that electrochemical reactions conducted at the active electrode during operation provide species which do not interfere with or compete with the selected ionic species for transport (i.e. the target or therapeutic ion species). For example, if the drug to be delivered is positively charged, and it exists in the reservoir as a hydrochloride salt, the active electrode will be the anode. If a silver (or silver/silver chloride) electrode were used as the anode, then during operation of the electrode, a positive ion species formed at the anode would be silver cations. The reservoir includes chloride ions in solution from the hydrochloride salt of the drug, so silver chloride (which is insoluble) would be continuously formed during electrode operation. The silver chloride would precipitate from solution, at the surface of the active electrode. The result, then, would be continuous operation of the electrode to provide electromotive force to the cationic drug ion, without addition of positively charged species, (i.e., silver cations as extraneous cations) to the anodic reservoir in a mobile form. Thus, the concentration of extraneous ions in the active electrode reservoir is maintained at a minimum, or at least is not increased through operation of the system.

It is not, in practice, practical to completely exclude extraneous ion from typical electrotransport systems. The reasons for this include the fact that the hydrophilic reservoirs (typically aqueous systems involving gels or gel matrices) often may include therein, in addition to the drug species to be delivered (or a precursor for the drug species to be delivered) buffers, antibacterial agents, etc. Further, it may just be impractical in many instances to provide for a complete absence of ions (other than any ions to be selectively transported) and complete suppression of formation of such ions during electrode operation. Thus, even if the methods of Phipps et al. '787 and '819 are practiced to avoid introduction of more extraneous ions into a system, typical iontophoresis systems will in general include, ab initio, a significant concentration of extraneous ions. As will be seen in discussions below, this concentration of extraneous ions can have a significant effect on the performance of the iontophoresis process. In some instances it will negatively effect the process.

SUMMARY OF THE INVENTION

The present invention generally concerns controlled environment electrotransport techniques and methods, and also apparatus for conducting controlled environment electrotransport processes. The term "controlled environment electrotransport" and variants thereof, as used herein, refers to electrotransport methods wherein the ionic content of the active electrode reservoir is selectively controlled, to achieve desired results. Examples are to maintain control of ionic content to selectively control rate of delivery of target species, or to control environmental parameters such as pH or conductivity. In certain preferred applications the electrotransport technique involved will be iontophoresis, so the process would generally be a controlled environment iontophoresis.

In general, methods of conducting controlled environment electrotransport according to the present invention comprise conducting electrotransport with: selected operation of a primary electrode arrangement to provide electromotive force for transport of target species from an active electrode reservoir; and, selected operation of a secondary electrode arrangement, different from (or in a different manner than) the primary electrode arrangement, to selectively affect relative concentrations of ions in the active electrode reservoir. In general, the secondary electrode arrangement may be operated continuously or periodically. The secondary electrode arrangement may be operated while the primary electrode arrangement is operated, or, in some applications, it may be operated while no current flows through the primary electrode arrangement. In those applications in which both the primary electrode arrangement and the secondary electrode arrangement are operated at the same time (at least part of the time) relative current flow through the primary electrode arrangement and the secondary electrode arrangement may be varied, during the process. Either may carry the higher percentage of current, at any given time. Both may be conducted as anodes, both as cathodes, and in some applications one as the anode and the other as a cathode.

Herein the term "electrotransport", "transport" and variants thereof, in this context, refers to transfer of ions from the active electrode reservoir, by means of applied electromotive force. Losses of ion content through other means, for example diffusion, or electrochemical change, are not generally included within this utilization of the terms. In general, the methods are particularly well adapted for conducting electrotransport wherein the active electrode reservoir includes target species and extraneous ion species; and it is particularly useful for applications wherein the target species is charged (i.e., is ionic). Herein the term "target ion species" refers to therapeutic ions or other ions to be transferred from the electrode reservoir, for medical purposes. For example, the target ion species may be a drug species to be delivered to a patient, a precursor for such a drug species, a therapeutic metal ion species, a species utilized in some form of diagnostic procedure, or a species used to facilitate the electro-osmotic delivery of uncharged therapeutic agents. The target ion species may be either a cationic species or an anionic species, depending upon the system of concern. The term "extraneous ions" generally refers to ions other than the therapeutic or target species in the active electrode reservoir which will feel the electromotive force for delivery to the subject, during electrode operation. If the target species is ionic (i.e., the process is iontophoresis), extraneous ions are ions of an analogous charge (in sign) to the target ion(s), but different from the target ion(s).

In some preferred applications the secondary electrode arrangement is operated to selectively maintain a level of a particular extraneous ion species in the active electrode reservoir as a constant. For example, it may be operated to maintain a constant pH (i.e., hydronium ion content) in the active electrode reservoir. Herein, when it is said that the concentration of a species is maintained substantially constant, it is meant that it is preferably maintained at a particular value ± about 30.0% of that value, and more preferably ± no greater than about 10.0% of that value.

In some preferred applications of the present invention, the secondary electrode arrangement is operated to electrochemically introduce into the active electrode reservoir a species which is also being lost, due to diffusion and/or the electromotive force applied to the active electrode reservoir for transport of ions therefrom.

In some preferred applications, it may be desirable to replace lost extraneous ions at the very same rate they are lost, for example to maintain constant pH as indicated above. In other instances, it may be desirable to replace them at a rate different from their loss, in order to achieve some desired effect. For example, if the rate of loss of extraneous ions, due to electromotive force supplied by the primary electrode arrangement, is such as would undesirably affect the rate of delivery of the target species (if not accounted for), the secondary electrode arrangement can be operated in order to replace the lost extraneous ions at a rate so as to maintain a desired rate of delivery for the target species. A specific example of this, as will be seen from detailed descriptions below, is operation of the secondary electrode arrangement, during iontophoresis, in a manner to maintain a constant molar fraction of a target ion species within the active electrode arrangement.

Herein when it is said that a molar fraction of a target ion is maintained at a substantially constant level, it is meant that it is preferably maintained within about 30.0%, more preferably within about 10.0%, of that level throughout the electrotransport process.

As will be seen from the detailed descriptions, in some preferred applications it may be useful to operate the secondary electrode arrangement to remove extraneous ions. In still other applications, it may be desirable to operate the secondary electrode to change the presence (i.e., by removal or addition) of the target species. Herein when it is said that the secondary electrode arrangement is operated to affect the presence of a species (by removal or addition) it is meant by means other than, or in addition to, mere transport to the subject or elsewhere. In addition, it is meant that the effect is different from that resulting from the primary electrode arrangement.

In preferred applications, the processes are conducted in a manner such that total current flow through a subject of the iontophoresis is maintained substantially constant. That is, current flow between the active electrode reservoir and the companion electrode reservoir, by passage through the subject, is maintained substantially constant. Herein when it is said that the total current flow is maintained substantially constant, it is meant that it is maintained within about 30.0% of a particular figure, more preferably when at about 10% of that figure, throughout the electrotransport process. Maintenance of a constant current flow may be conducted by adjustment, as necessary, of relative current flow between the primary electrode arrangement and the secondary electrode arrangement, within the active electrode reservoir.

A preferred apparatus according to the present invention, usable for conduction of processes according to the present invention, is an electrotransport apparatus comprising: an active electrode reservoir; a primary electrode arrangement in electrically conductive contact with the active electrode reservoir; and, a secondary electrode arrangement in electrically conductive contact with the active electrode reservoir, the secondary electrode arrangement being different from (or operably different from), and isolated from direct contact with, the primary electrode arrangement. The two electrode arrangements may be constructed for operation either at the same time or at selected times relative to one another. In some preferred systems, the arrangement includes means for selective, simultaneous, operation of both the primary and the secondary electrode arrangements. To be operable, both the primary electrode arrangement and the secondary electrode arrangement should be in electrically conductive contact with the electrolyte-containing medium, in the active electrode reservoir. The electrolyte medium in the active electrode reservoir may be an aqueous electrolyte-containing solution, or an electrolyte-containing gel or gel matrix, etc., as are commonly used in electrotransport.

Preferred apparatus includes a control means, for controlling current flow through the primary electrode arrangement and the secondary electrode arrangement. Preferably the control means includes means for maintenance of a constant current, if desired, through a subject of the electrotransport process.

Certain preferred apparatus include sensor means for detecting a selected characteristic of the active electrode reservoir. That selected characteristic may be, for example, total ion content, organic ion content, inorganic ion content, or content of some specific ion. It may also be, for example, means for detecting some physical characteristic of the electrolyte-containing material in the active electrode reservoir, which can be related to ion presence, for example, conductance. The sensor means for operation as described may include for example a pH meter, an optical sensor, an ion selective electrode, or a conductance measurement device. Preferably the sensor means is positioned in a portion of the active electrode reservoir immediately adjacent the skin surface of a subject of the electrotransport process, as measurement of ion concentration or electrolyte-containing solution characteristics immediately adjacent to a subject (i.e., adjacent to the surface through which transport occurs), is most important.

A preferred electrotransport apparatus generally usable in preferred iontophoresis processes according to the present invention includes: an active electrode reservoir including a concentration of target ions and a concentration of extraneous ions; and, means for maintaining a substantially constant rate of delivery of selected ions (typically target or therapeutic ions for iontophoresis) from the active electrode reservoir, during operation of the apparatus. This means may be provision of arrangement including a primary electrode system and a secondary electrode system, as described above, when coupled with appropriate control means. In particular, the control means and primary and secondary electrode system should be such that a molar concentration of the target ions for transport can be maintained substantially constant, throughout the iontophoresis process. Preferably means are also provided, to control the rate of delivery of the target species, while maintaining a constant current flow through the subject of the iontophoresis process.

Another preferred electrotransport apparatus according to the present invention includes: an active electrode reservoir including a concentration of target species and a concentration of extraneous ions; and, means for maintaining a concentration of a selected extraneous ion species in the active reservoir substantially constant, throughout operation. An example would be maintenance of constant pH, through use of a secondary electrode arrangement. A particular preferred such arrangement is one wherein the secondary electrode arrangement is an iridium oxide arrangement; i.e. an electrode operable for oxidation/reduction reactions of Ir(III) and Ir(IV). If desired, a pH sensor feedback arrangement can be used to facilitate control.

In some preferred applications, the two electrodes in a delivery reservoir can be used to facilitate disposal of the reservoir at the end of a delivery process. For example, they can be operated to render any residual drug species therein inactive, for convenient disposal. Either pre-programming or sensor means can be used to facilitate this process.

In some applications, techniques and apparatus described herein may be used to facilitate passive delivery of species (i.e. delivery through diffusion rather than electrotransport) by operation of primary and secondary electrodes in a reservoir to control the concentration of diffusible species in the reservoir. For example, if a drug species has a charged form and an uncharged form, and the uncharged form of a drug species is more mobile (through diffusion) than the charged form, the techniques described can be used to control pH of the reservoir to control concentration of (and hence rate of delivery of) the uncharged form. Such a process would not necessarily concern electrotransport, but it would be an advantageous application of principles described herein.

The principles of the present invention may be applied to a system involving pulsed operation; for example, wherein pulses of current pass through the subject.

Further regarding general processes and advantages to the present invention will be understood from the following detailed descriptions. The descriptions are intended to be exemplary of the general principles of the invention, not otherwise limiting of the general applications and principles of the present invention. It is noted that in the drawings in some instances relative material or component thicknesses or sizes may be shown exaggerated, to facilitate understanding.

BRIEF DESCRIPTION OF THE DRAWINGS

FIG. 1 is a graph indicating change in the rate of delivery of a particular drug species, with time, for four different systems involving extraneous ions; the experiment to which FIG. 1 is related being described in Experiment 1.

DETAILED DESCRIPTION OF THE INVENTION

A. Some General Observations Regarding Iontophoresis

Figure 1:
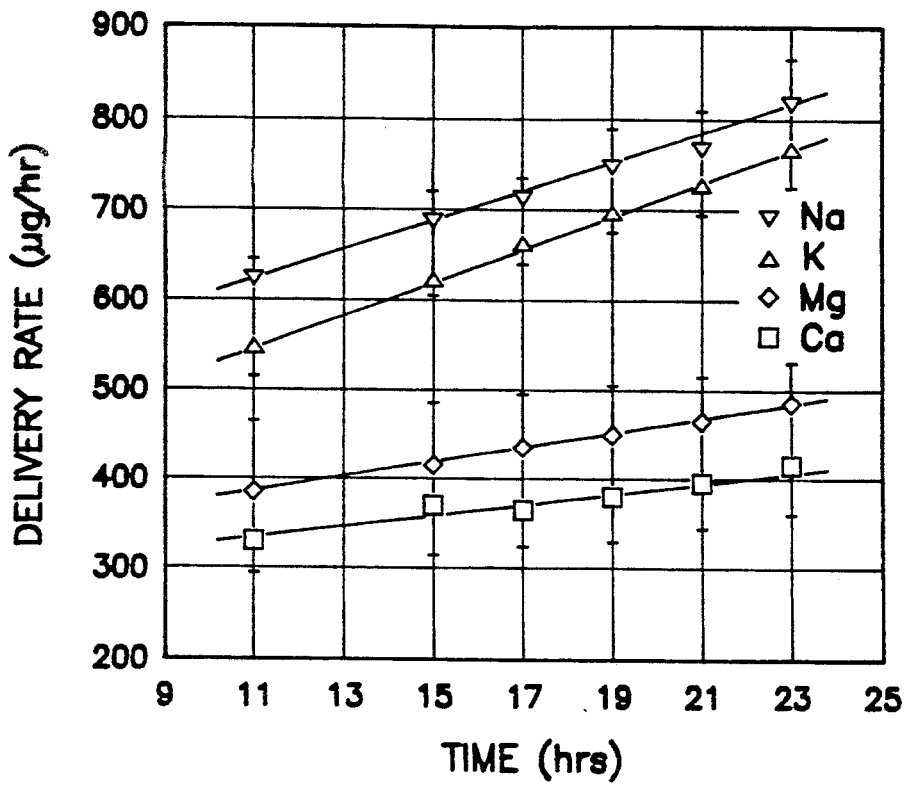

The methods and apparatus of the present invention in part developed as a result of, and in response to, certain general observations made with respect to iontophoresis and iontophoretic devices. In this section of the discussion these general observations, and basic principles concerning them, are discussed. Detailed descriptions with respect to experiments conducted, to develop the reported observations and principles, are provided in the experimental section at the end of this disclosure. General details and descriptions concerning methods and apparatus according to the invention, are provided in the next section of this detailed description.

1. Relationship Between Current and Drug Delivery for an Iontophoretic System Involving Little or No Extraneous Ions in the Active Reservoir Herein the term "extraneous ions" has generally been used to refer to ions of the same charge (sign) as the material (for example drug or drug precursor i.e. the target or therapeutic species) to be delivered from the active electrode, and present in the reservoir of the active electrode, when the target species is charged. For a positively charged drug species "D+", or a target species delivered from a reservoir of the anode, extraneous ions would be various cations (other than the target species) in the solution of the active electrode, for example extraneous metallic cations. All other cations, besides the target cation, will be referred to herein as extraneous ions, regardless of whether or not they carry the same absolute charge value.

The rate of delivery of the drug ion from the active electrode reservoir and across the skin membrane (in the absence of extraneous ions in the reservoir) is generally the sum of that amount of transfer which occurs as a result of diffusion plus the amount of transfer (i.e. electrotransport) which occurs as a result of applied electromotive force (i.e., applied voltage). In this discussion diffusion processes will generally be ignored as they do not concern the applied force, but rather are controlled by relative concentrations of the species on opposite sides of the skin barrier.

In general, the amount of transport which occurs as a result of applied voltage is directly proportional to the amount of current passing through the cell. Thus, in general, if the amount of current is doubled, the rate of transport due to the electromotive force is also doubled; see, for example, Padmanabhan, R. V. et al., "In vitro and In vivo Evaluation of Transdermal Iontophoretic Delivery of Hydromorphone", *J. Controlled Release* Vol. 11, pages 123-135 (1990), the disclosure of which is incorporated herein by reference.

In practice, then, the amount of current can be utilized to control the rate of drug delivery. This can generally be done in either or both of two manners: change in the potential (voltage) applied between the active and ground electrodes; or, change in resistance to passage of current between the two electrodes. In practice, typically resistance to ionic conduction between the two electrodes decreases, as the electrolytic material in the electrode reservoirs begins to permeate the skin. That is, in practice there is observed a lower resistance to current passing between the two electrodes, with passage of time. Thus, over a sustained period of time, for a typical iontophoretic system with little or no extraneous ions, constant rate of target ion delivery or transport can be maintained with a lowering of voltage, at least over a given range of concentrations of drug ion in the active reservoir, wherein the concentration is not modified greatly and is above a threshold level determined by physical/chemical properties of the transported species and tissue through which transport occurs. With respect to this threshold level, reference is made to the principles described in the next section herein.

2. The Effect of Concentration of Drug Ions on Rate of Drug Delivery at Constant Current In general, although rate of drug delivery is proportional to current, at a constant current the rate of drug delivery ($R_d$) is independent of drug concentration (i.e. target species concentration) in the active electrode reservoir, provided that the concentration is at least above a threshold level (and little or no extraneous ions are present); see Padmanabhan, R. V. et al. *J. Controlled Release*, supra.

3. Effect of Charge on Migrating Species

If charged at all, the migrating species may be of a variety of charges. For example, if the migrating species is a metallic cation, it could be a cation which has a +1 charge (for example potassium or sodium ions) or it could be a metallic cation which has a +2 (or some other) charge (for example calcium or magnesium ions). In general, assuming otherwise similar mobility through the skin surface, for a given current the species having the greater charge will be less mobile. An explanation for this should be apparent. In order to satisfy maintenance of a constant current, twice as many +1 charged species would have to pass through the skin, than would +2 charged species. Thus, in two different systems, a first system involving species of a +1 charge and a second system involving species of a +2 charge, if a constant (and the same) current were maintained in each system (and mobilities were otherwise the same), the system involving ions of a +1 charge would have twice the rate of delivery, to maintain the same current. See, for example, Phipps, J. B. et al., *Solid State Ionics*, supra.

4. Effect of the Presence of Extraneous Ions in the Active Electrode Reservoir The presence of extraneous ions, as defined herein, in the active electrode reservoir will have a profound and significant effect on the above related principles and observations. In general, this may be understood by considering a hypothetical system. Assume for the moment a system in which a constant current is maintained. The ionic transport needed to maintain that current can be satisfied by any of the appropriately charged ionic species present in the active electrode reservoir being transported into the skin therefrom (or for that matter by ions of an opposite charge being transferred into the active electrode reservoir from the skin). Thus, transport of either the drug ion (if charged) or the extraneous ions from the active electrode reservoir will satisfy the flow of current. Alternately stated, both the "target" species and (if ionic) the "extraneous" species in the active electrode reservoir will feel effects of the applied electromotive force. (However, if the target species and extraneous species are charged with the same sign but to a different degree, they will feel a different force as described above.)

Mobility of any given species will in part be a function not only of its charge, but also its molecular weight, size, charge density, etc. Thus, in general, the target species and the extraneous ions will not have the same mobility, (nor the same delivery rate) for a given current.

The consequences of this may be understood from a hypothetical example involving further assumptions. Assume, for example, that the target species to be delivered is a relatively large organic drug species carrying a +1 charge, for example hydromorphone cation (HM$^+$) resulting from dissociation (ionization) of hydromorphone hydrochloride, i.e, the species is protonated hydromorphone. Assume further that the extraneous species present in the active electrode reservoir, along with the hydromorphone species, is a small highly mobile +1 charged species, for example sodium ions. Under constant applied current, due to greater mobility, it can be expected that the rate of delivery of the extraneous ions will be greater than the rate of delivery of the hydromorphone ion. This means that the concentration of the extraneous ions present in the active electrode reservoir will drop more rapidly than the concentration of the target species, hydromorphone.

Of course the rate of total ion transfer (i.e., rate of extraneous ion transfer plus rate of target species transfer) will remain generally constant, for a constant current, provided the threshold level of ion concentration is exceeded, under the general principles discussed above in paragraph 2 of this section. However, since the concentration of extraneous ions is decreasing more rapidly than the concentration of target species, in time the relative rates of transfer of the two will change. More particularly, the absolute rate of transfer of extraneous ions, in time, will decrease and the relative rate of transfer of target species will increase.

The above may be alternately stated, in a general form, as a principle that the rate of delivery of any given species, under an applied voltage in an iontophoretic system, (electrotransport system in which the transported species is charged) will be dependent on the fraction of the total transportable ionic species (i.e. target species plus extraneous ions) represented by that target species (assuming all species have the same charge, if they do not a factor for mobility difference due to a charge difference would be included in the formula). Thus, for a system of mixed ions the rate of delivery of a target ion "$T_i$" in the presence of extraneous ions "$X_i$", under conditions of constant current, will be dependent on the fraction $[T_i]/([T_i]+[X_i])$. This fraction will be referred to herein as the "molar fraction" or "charge equivalent fraction", of the species $T_i$ where $[T_i]$ is the molar (or charge) concentration of $T_i$ and $[X_i]$ is the molar (or charge) concentration of $X_i$, in the active electrode reservoir. The term "molar fraction" as used herein will be understood to include a correction for equivalents of charge. For example, $[X_i]$ as used in the formula will be equal to 2 times the concentration of species $X_i$, if $X_i$ carries a charge value of 2, i.e., +2 or −2. The same will be true for $[T_i]$. It is noted that mobility of any species is not only determined by charge state, but also molecular weight, hydrophilic nature and charge density, as well as degree of interaction with the tissue (skin).

A general principle which can be derived from above is that: if the active electrode reservoir includes therein both a charged target species and extraneous ions; and, if the target species and extraneous ions do not possess identical mobilities, in time, under a given applied voltage (i.e., galvanostatic conditions), the rate of delivery of the target species will change. Whether it increases or decreases will depend upon whether the target species is less mobile or more mobile than the extraneous species. This principle will hold regardless of whether: the active electrode is operated as an anode or cathode; the target species is positively or negatively charged; the target species and the extraneous ions bear equivalent charges; the applied potential is constant or varied in time; and, the current is constant or varied in time; etc. The reasons for this include the fact that the phenomenon generally results from differences in mobilities between the charged target species and the extraneous species.

The above asserted principle can be demonstrated experimentally. The specific experimental details for demonstration of this is provided hereinbelow, at Experiment 1; the data for which is reported in FIG. 1. In general, FIG. 1 provides the delivery rate in micrograms per hour of a target species (hydromorphone cation) in an iontophoretic system under four different circumstances. More particularly, four systems were prepared in which the active electrode reservoir (the anode reservoir) initially included a selected concentration of hydromorphone, and a selected concentration of one of four extraneous ions, i.e., the four experimental runs each involved one of calcium ($+2$), magnesium ($+2$), potassium ($+1$) or sodium ($+1$) ions, as the extraneous ions. Throughout the experiment, a constant current of approximately 1 mA (milliamp) was maintained. As can be seen from FIG. 1, in each instance the rate of hydromorphone delivery, under conditions of constant current, was found to increase in time. The reason for this, again, is the general principle enumerated above that:

(a) Since the smaller extraneous ion species (whether $Ca^{+2}$, $Mg^{+2}$, $K^{+1}$ or $Na^{+1}$) is more mobile than the relatively large organic hydromorphone species; and (b) Since the rate of transfer of the drug species (hydromorphone), under constant current, is a function of the concentration of the target species divided by the charge concentration of the target species plus the charge concentration of the extraneous ions, then, (c) as the concentration of the extraneous ions $[X_i]$ decreases more rapidly than the concentration of the hydromorphone ions $[T_i]$ described below, the ratio represented by the function (for molar fraction or charge equivalency fraction) increases, and thus the rate of delivery of the target species increases. (In other words, in time the molar fraction of $T_i$ increases and the delivery rate ($R_d$) of $T_i$ also increases.)

It is noted that for the experimental data reported in FIG. 1, the increase in the rate of the hydromorphone for each of the four systems was linear. This could be expected for a system in which throughout the experiment both the concentration of the target ion and the extraneous ions is maintained above the threshold level.

5. Problems Resulting from the Above General Principles and Observations

The above general principles and observations present a significant problem, to practical application of iontophoresis techniques. If the active electrode reservoir were maintained completely free of extraneous ions, generally no problem would be presented. However, as explained above, generally this cannot be readily accomplished at least for the reasons that: the presence of extraneous ions may be desirable due to the need, for example, for buffered systems, systems involving additives such as antibacterial agents etc., systems wherein biocompatability is favorably influenced by introduction of selected ions; and, the general difficulty of obtaining extraneous ion-free electrode reservoirs. Thus, while the basic principles from the Phipps et al. U.S. Pat. Nos. 4,747,819 and 4,744,787 could be applied to avoid further generations of extraneous ions during the iontophoretic process itself, developing extraneous ion-free reservoirs in the first instance, can be relatively difficult or for other reasons undesirable.

On the other hand, if the active electrode reservoir is not extraneous ion-free, precise or satisfactory control over drug delivery rate can be difficult, if not impossible, to achieve. Further, and in particular, for such a system it may be desired that the drug delivery rate be maintained constant, which, for conventional systems, has been nearly impossible to achieve. For example, in a system in which the extraneous ions are more mobile than in the drug ion, under a constant applied current, delivery rate of the drug ion will increase in time, as indicated above. The rate of delivery of the drug ion could be decreased, to counterbalance this, by decreasing the applied voltage (i.e., decreasing the current). A problem with this, is that any changes in the current from the electrode will not only effect the rate of delivery of the drug ion, but also the rate of delivery of the extraneous ions as well, so the imbalance will be regenerated. Thus, continual modification in the amount of current would be necessary, to obtain precise control over the rate of delivery of the therapeutic agent. Also, it may be found that control over the current sufficient to maintain a constant rate for and extended period of time may be impossible to achieve, due to limits based on the highest current acceptable and lowest current acceptable to the patient under the conditions of iontophoresis. Also, with multiple variables such as concentration of extraneous ions, concentration of the therapeutic ions, etc. being involved, calculation of appropriate levels for precise control may be difficult. Of course if a huge excess (relative to drug ion) of extraneous ions were used, the differences in mobility would be less important; however, the molar fraction of the target ion would be so low that iontophoresis would be inefficient. Also, if the active electrode reservoir were constantly replenished with fresh electrolyte (i.e., it were not a "closed" reservoir") the molar fraction of $T_i$ would be constant; however, such a system would be cumbersome and inconvenient.

B. General Methods of the Present Invention

The present invention, inter alia, concerns methods applicable to obtain selective control over delivery rate of a target ion or therapeutic ion, $T_i$, in the presence of extraneous ions, $X_i$, in an active electrode reservoir. The methods may also be used to maintain a selected ion species at a desired concentration, to advantage, for example to enhance target species stability or biocompatibility. The methods of the present invention are generally referred to herein as methods for controlled environment electrotransport.

More specifically, the methods are particularly well adapted for use in association with a "closed" reservoir system, i.e., a reservoir system which is initially prepared with a particular volume of ion containing solution (or gel) where that solution or gel is not continually replenished from an essentially unlimited supply. A basic step in applications to the methods is to provide for adjustment in the presence of selected ions in the active electrode reservoir, in time, in a selected manner.

1. A Basic Step of Certain Preferred Applications: Selective Generation or Removal of Extraneous Ions to Desirably Effect [$X_i$] During Iontophoresis When conducted according to the present invention, preferred methods of iontophoresis will include steps for selected modification in the presence of extraneous ions in the active electrode reservoir. Adjustments in the presence of extraneous ions may take either of two forms, depending upon the system: (a) addition of extraneous ions to the system; and, (b) removal of extraneous ions from the system. In general, this may be done to obtain (or maintain) a desired molar fraction of target ion, $T_i$, during the iontophoresis or for maintenance of constant cell conditions, for example pH. That molar fraction of $T_i$ may be maintained as a constant, for a constant rate of delivery of $T_i$, or increased or decreased as desired.

(a) Addition of Extraneous Ions to the Active Electrode Reservoir

It will be desirable to control the active electrode reservoir environment by addition of extraneous ions to the active electrode reservoir, either continuously or periodically throughout the iontophoretic operation (i.e., during passage of current through the active electrode reservoir and during electrotransport), under at least any of three conditions: (i) extraneous ions in the reservoir are more mobile than the target or therapeutic ion, and thus their continual depletion is leading to an undesired increase in rate of target ion delivery; (ii) under conditions of operation of the iontophoretic system extraneous ions in the active electrode reservoir are being depleted by means other than electromotive transport (through the skin) therefrom, again leading to an undesired rate of increase in delivery of target ions; or, (iii) regardless of the method of loss, extraneous ions are lost and it is desired to maintain their presence constant, an example of this latter being constant pH. Any of these may be referred to by the general phenomenon that it may be desirable to add, either continuously or periodically, extraneous ions to the active electrode reservoir throughout the operation of iontophoresis, in response to what would otherwise be an unacceptable depletion or rate of depletion, in time, of the concentration of extraneous ions within the active electrode reservoir.

(b) Removal of Extraneous Ions from the Active Electrode Reservoir

Similarly, it may be desirable to selectively remove extraneous ions from the active electrode reservoir, either continuously or periodically during the conduction of iontophoretic process, under at least any of three conditions: (i) the target ion is more mobile than the extraneous ions, thus the rate of depletion of the target ion is dropping in time as its concentration reduces, rapidly, relative to the concentration of extraneous ions; (alternately phrased the molar fraction of $T_i$ decreases in time); (ii) electrochemical reactions within the active electrode reservoir lead to an undesirable increase in the concentration of extraneous ions in time again leading to a decrease in the rate of delivery of $T_i$; or, (iii) regardless of how, [$X_i$] is increasing, and it is desired that it be maintained constant, again an example of this letter being constant pH which can be affected by removal of hydronium ions ($H^+$) or hydroxyl ions ($OH^-$).

2. The Preferred Method of Modifying the Presence of Extraneous Ions in the Active Electrode Reservoir: Operation of a Second Electrode Therein In preferred applications of the present invention, the presence of extraneous ions in the active electrode reservoir is modified either periodically or continuously throughout the electrotransport process (i.e., while electrotransport into a subject of the process is conducted), through operation, in the active electrode reservoir, of a second or secondary electrode system. That is, in addition to the primary electrode system of the iontophoresis system, in contact with the active electrode reservoir and selectively operated during iontophoresis, a secondary electrode system is provided. The secondary electrode system can be operated, as desired, to selectively effect extraneous ion presence and concentration. Of course, operation of the secondary electrode system may also cause electrotransport in some systems.

(a) The Addition of Extraneous Ions

A secondary electrode system capable of producing extraneous ions could be placed in the active electrode reservoir, and continuously or periodically operated to generate extraneous ions, providing a feed to the active electrode reservoir. For example, assume that the appropriate extraneous ion for introduction to the active electrode reservoir, to replace some depleting extraneous ions during the iontophoresis process, were hydronium ions. If the secondary electrode placed in the active electrode reservoir of the iontophoresis process was one that was capable of producing hydronium ions, selectively, when a current is passed therethrough, it could be operated either continuously or periodically, to generate hydronium ions replacing those lost. In the alternative, or in addition, if the extraneous ion being lost from the active electrode reservoir during iontophoresis were sodium ions, a sodium tungstate intercalation-type electrode could be provided as a secondary electrode, and operated as an anode. If the extraneous ion being depleted during operation of the iontophoresis cell were $Cu^{+2}$, a copper electrode operated as an anode, capable of releasing $Cu^{+2}$ upon passage of current therethrough, could be provided in communication with active electrode reservoir and periodically or continuously operated to produce extraneous ions. It will be understood that the three examples (hydronium ion, sodium ion and copper ion generation) given were meant to be representative and not limiting.

In general, it will not always necessarily be desirable to generate extraneous ions at the same rate they are depleted, due to transport. That is, it will not necessarily always be desirable to maintain [$X_i$] constant. A reason for this is that if [$X_i$] were constant, and [$T_i$] were decreasing, then the $R_d$ (rate of delivery) of $T_i$ would decrease; and $R_d$ for $X_i$ would continually increase. Thus, the efficiency of iontophoresis would reduce in time. Of course in some instances it may be desireable to maintain [$X_i$] constant, for example a relatively constant pH might be maintained for patient comfort and system biocompatability or to maintain stability of some species in the reservoir. The concept of biocompatibility is generally discussed in Molitor, H. et al, *Am. J. Med. Sci.*, Vol. 198 pp 778–785 (1939), the disclosure of which is incorporated herein by reference.

The electrode system for adjusting or modifying extraneous ion presence should be a different electrode system than (or a system operated to different effect from) the primary electrode system for the iontophoresis. That is, in applications of the present invention two different electrode systems are provided in electrical contact with the active electrode reservoir, one of which is for selective operation to affect the presence of $X_i$ independently of $T_i$. Details concerning this are provided in apparatus discussions below.

Herein when it is said that the secondary electrode system is "different" from the primary electrode system, it is meant that the effect of electrochemical reactions generated thereby, on the ionic content of the active electrode reservoir, are different, i.e., an effect in addition to (or as an alternative to) mere electromotive effect, and different from the electrochemical effect of the primary electrode, is provided by the secondary electrode. The particular and desired effect of each will depend upon the system of interest, with each being chosen to perform in a selected manner to achieve the desired effect. In some systems both electrode systems may comprise identical materials, one system being operated as an anode, the other as a cathode. Since their effects on the ionic content of the reservoir would be different, they would be "different" systems according to the above definitions.

(b) Removal of Extraneous Ions from the Active Electrode Reservoir

In contrast to the methods of the previous section, under some circumstances it may be desirable to operate a secondary electrode system in communication with the active electrode reservoir in a manner such that extraneous ion presence is reduced. For example, if it is desirable to remove $Cu^{+2}$ from the active electrode reservoir, in order to maintain a desired delivery rate of target species, a secondary electrode system capable of removing $Cu^{+2}$ from the active electrode reservoir could be used. An example of this would be to operate a copper electrode therein as a cathode, plating copper ions from the active electrode reservoir thereon as copper metal. If the extraneous ion were a sodium cation, its presence could be reduced by operation of a sodium tungstate electrode as a cathode. These examples will be understood to generally exemplify methods of the present invention whereby extraneous ion concentration is reduced.

3. Alternate Method: Operation of the Secondary Electrode System to Modify Concentration of the Target Species It will be apparent that if the important ratio to control the rate of delivery of the target species is the concentration of the target species ion relative to total ion content (i.e. molar ratio of target ion), then control over that ratio can be maintained by either: modifying the presence of extraneous ions, as described in section B2 above; or, by modifying the presence of target ions; or, both. For many systems, modification of the concentration of target ions will be less desirable, as it would concern modifying the presence of the key species to the therapeutic process. However, in some applications it may be desirable. For example, if the concentration of extraneous ions is reducing, in time, at a rate greater than the change in concentration of the target species, leading to the tendency for an increase in the rate of target species delivery across the skin barrier, the ratio of $[T_i]$ to $([T_i]+[X_i])$ could be modified by reducing, either periodically or continuously, $T_i$, without transport, to maintain the ratio at a desired figure. A variety of manners of operations of the secondary electrode could be utilized to accomplish this depending on the system. For example, if the target species were a metal cation, the secondary electrode could be operated as a cathode selected for removal of that particular species from the system. If the target species were a particular organic cation, the secondary electrode could be operated either in a manner to produce an anion for that organic cation, which, in combination with the organic cation, forms an insoluble precipitate in the reservoir, thus effectively reducing concentration of $T_i$ available for electromotive transport; or, in a manner which destroys (or otherwise renders inactive) the organic species, again effectively reducing concentration of $T_i$ available for transport.

4. Operation of the Secondary Electrode System as an Anode or Cathode

Whether the secondary electrode system is operated as a cathode or anode depends, primarily, on the nature of the electrochemical reactions to be precipitated thereby, and not whether the primary electrode system in the same reservoir is itself operated as an anode or cathode. That is, if the primary electrode system is operated as an anode, the secondary electrode system may be selectively operated as either an anode or cathode, depending upon the reactions to be initiated thereby. In addition, if the primary electrode system is operated as a cathode, the secondary electrode system may be operated as either an anode or a cathode, again depending upon the reactions to be precipitated thereby. If the secondary electrode system is operated analogously to the primary electrode system (i.e., both as anode or both as cathode) then the companion electrode for each will be the remote, ineffective, or ground electrode of the iontophoresis system. If, on the other hand, the secondary electrode system is operated in an opposite manner with respect to current flow from the primary electrode system (i.e., one as an anode and one as cathode) and both are operated at the same, time then the secondary electrode system, will, at least in part, involve current flow with the primary electrode system (i.e., between the primary and secondary electrode systems, the direction of current flow depending on which is the anode).

What is generally required is: that the secondary electrode system be provided out of "direct" electrical contact with the primary electrode system, i.e. the secondary electrode should be isolated (spaced) from the primary at least by the electrolyte material of the reservoir; and, that the secondary electrode system be provided in appropriate electrical communication with the electrolyte solution (gel or gel matrix) of the active electrode reservoir. Specific arrangements for accomplishing this are described herein below, where preferred apparatus is described.

5. Relative Amount of Current Flow Through the Primary Electrode System and the Secondary Electrode System Herein, the term "primary electrode system" has been utilized to refer to the electrode system which in general, would have defined the electrotransport system of concern if the system were conventional; and, the term "secondary electrode system" has been utilized to refer that electrode which is selectively operated to selectively adjust the presence of, or relative concentrations of, target ions and/or extraneous ions in the active electrode reservoir (without transport or in addition to transport). This may be done, for example, in response to undesired changes in ionic content of the reservoir, for example those precipitated by operation of the primary electrode system. The term "undesired changes" in this context generally includes within its scope changes in the molar ratio which in some undesirable manner affects rate of delivery (Rd) of the target ions, and changes that undesirably affect stability of the reservoir, patient comfort or system biocompatibility. The term "without transport" in this context means a change in ion presence accomplished without transport of the ion through to the subject of the iontophoresis; i.e., without transport across the skin. By the use of the terms "primary" and "secondary" in this manner, there is no intention to suggest that there is some necessary or preferred relative amount of current to be passed through the two electrode systems. That is, in operation of electrotransport apparatus, according to the present invention, the majority of the current may be carried by the primary electrode system, or it may be carried by the secondary electrode system, or the ratio or relative amounts may change during the operation. In general, this will depend upon the amount of electrochemical change that must be precipitated by the secondary electrode system in order to achieve the desired relative concentrations of $T_i$ and/or $X_i$ in the system, or to achieve the desired effect on $[T_i]$ and/or $[X_i]$. In some systems it may be appropriate to have no current flow through the primary electrode system, while the secondary electrode system is operated. This will, in part, depend upon at least: the effect of the secondary electrode system on transport; and, the need for, or desirability of, maintenance of constant transport.

It should also be noted that the terms "primary electrode system" and "secondary electrode system" are not necessarily utilized to refer to electrodes in the singular. That is, the primary electrode system may comprise a single electrode or a plurality of electrodes; and, the secondary electrode system may involve a single electrode or a plurality of electrodes. Further, electrodes in addition to the primary electrode system and the secondary electrode system may be utilized in some situations.

6. A Preferred Application: Maintenance of a Constant Rate of $T_i$ Delivery ($R_{dTi}$)

In many applications of iontophoresis where extraneous ions are present in the active electrode reservoir, it may be desirable to merely maintain the rate of delivery ($R_d$) of the target or therapeutic ion, $T_i$, as constant. If, as explained for hypothetical above, the target ion $T_i$ is less mobile than the extraneous ion $X_i$, under conditions of constant current, in time, the $R_d$ of $T_i$ will increase because of the rate of depletion of the more mobile extraneous ions is greater than the rate of depletion for the less mobile target ions. That is, with time the molar fraction of $T_i$ increases. For such a system, it may be desired to maintain the rate of delivery of the target ions constant. This can be readily achieved by, in time, replacing the extraneous ion $X_i$ at a rate sufficient to maintain the molar ratio of $T_i$ constant. This will be a rate slower than the $R_d$ of $X_i$, since $[T_i]$ is constantly reduced, in the closed reservoir system. Maintenance of relatively constant molar fraction of $T_i$ can be accomplished, for example, by operation of the secondary electrode, on a periodic or continuous basis, with sufficient current to produce extraneous ions in the system as necessary. Herein, when it is said that the molar fraction of a species such as $T_i$ is maintained substantially or relatively constant, it is meant that it is preferably maintained within about 30.0% of its original or a preselected value, more preferably within about 10.0%, throughout the iontophoresis process. In general, the need to maintain the molar fraction of a target species within some specified value will be related to the therapeutic index of a species. It will be understood that the present invention is well suited to applications wherein a high degree of control is necessary.

In general, a constant rate of delivery of $T_i$ can be maintained in some systems without replacement of the very same extraneous ions as are lost, if the extraneous ions that are put into the system have approximately the same mobility, relative to the target ion $T_i$, as do the original extraneous ions in the system. For example, if the original extraneous ions in a system are sodium ions, and the original target ion in the system is a large, relatively immobile, organic ion such as the hydromorphone ion, the extraneous ion put into the system with time, by the secondary electrode, could be a sodium ion, but it also could be a similarly charged and similarly mobile ion.

Further, in some applications a constant rate of delivery of the therapeutic or target ion $T_i$ can be maintained even if the lost extraneous ions are replaced with extraneous ions of substantially different mobility, provided the current and/or rate of introduction of extraneous ions is adjusted to accommodate the different mobilities. For example, if an extraneous ion of a first mobility is being replaced (partially or completely), by operation of the secondary electrode, by an extraneous ion having twice the mobility, and if the rate of delivery of $T_i$ is to be maintained constant, then the rate of introduction of the new extraneous ion by means of operation of the secondary electrode should be provided at approximately one half of the rate of the loss of the initially present extraneous ion.

It will be understood that one problem with replacing (partially or completely) extraneous ions with different extraneous ions, is that the total transferrable ion pool in this system becomes modified in time, as it will eventually comprise a mixture of the originally present extraneous ions and secondarily introduced extraneous ions. Thus, operation of the secondary electrode after the initial introduction may have to take into account the plurality of extraneous ions present. There is no apparent reason why this cannot be accomplished, however, if appropriate model systems and/or calculations and/or methods of detection are used.

7. A Preferred Application: Maintenance of a Constant Concentration of an Extraneous Ion In some applications it may be desirable to maintain a constant concentration of an extraneous ion. This is the case, for example, if a constant pH is desired (e.g. to facilitate: drug stability; drug charge state, for example if the target ion is a polypeptide; and/or biocompatibility). In such circumstances, the secondary electrode can be chosen and operated to replace (or remove) hydronium or hydroxyl ions, as necessary, at the same rate they are depleted (or added) to the reservoir, by other means. Thus, constant pH could be maintained in a system in the absence of a pH buffer. This will be particularly useful in those situations in which the buffer could have deleterious effects on target ion delivery.

8. A Preferred Application: Maintenance of a Constant Total Current Passing Through the Subject In many systems it may be desirable to maintain a constant total current through the subject, during the electrotransport process. This may, for example, facilitate subject comfort and avoidance of undesirable side effects. It may also be convenient, in terms of chosen apparatus. If such an effect is desired, it may be necessary to provide appropriate electronic control of primary and secondary electrode systems, to effect a balance. For example, if operation of the secondary electrode system would otherwise involve an increase in current passing through the active electrode reservoir (and through the subject), its operation may be matched by a decrease in the current provided through the primary electrode system. Such a balance can be readily achieved with electronic circuitry presently available.

Herein, when it is said that an electrotransport system is operated at a "constant current" regardless of whether or not the secondary electrode system is in operation, it is generally meant that the current passing between the active electrode reservoir and the inactive electrode reservoir, i.e., through the subject, is preferably maintained at a selected constant value, plus or minus about 30.0% of that value. More preferably it is maintained at a constant value plus or minus less than about 10.0% of that value, throughout the process.

9. Determining the Rate at Which the Presence of Target or Therapeutic Ions $T_i$, or the Presence of Extraneous Ions $X_i$, Should be Selectively Modified by the Secondary Electrode (Either by Increase or Decrease in Presence of $X_i$ or by Increase or Decrease in Presence of $T_i$)

In general, certain preferred applications according to present invention involve selective operation of the secondary electrode in a preferred manner, in order to achieve the desired effect on the molar ratio of the target ions. In preferred, controlled, applications, then, it is essential to know what level of operation the secondary electrode is appropriate to achieve a desired effect. Guidance in this may be accommodated in either of two general manners: utilization of systems based upon model systems; or utilization of a feedback sensor arrangement in the active electrode reservoir.

(i) Model Systems

In typical applications, the electrotransport system will involve target species and extraneous ions, and concentrations of those species and ions, which will have been modeled and studied for that particular system, when operated under a selected current with respect to a selected type of subject. Thus, from model studies, it will be known to what extent, and under what conditions, the secondary electrode system should be operated. Operation of an electrotransport system with a subject, with known parameters and variables from models, is a matter of providing appropriate control of the various electrodes, throughout the iontophoresis procedure. This could be accomplished, for example, through a preprogrammed control system.

(ii) Use of a Feedback Sensor

In other systems, it may be desirable to adjust the operation of the electrodes, most notably the secondary electrode, in direct response to detected changes in the environment (for example ion content) of the active electrode reservoir. Such a system will be referred to herein as a "feedback" system and the means for detecting the change in the ion content of the active electrode reservoir will generally be referred to herein as the "feedback sensor" means or sensor means. The feedback sensor or sensor means may be utilized merely to detect a change, with the control system for the primary and secondary electrodes programmed to make a particular response in operation of the electrodes in response to a given detected change; or, a continual feedback system may be utilized, wherein the electrodes are operated by a control system to continually adjust, in order to maintain the feedback sensor measurement at a preselected value.

A variety of sensor means may be utilized, and in general, the means chosen will depend upon the particular electrical system and electrochemical reactions involved. For example, if hydronium or hydroxide ions are the extraneous ions content of concern, the feedback sensor may be a pH sensor of any variety of types. Other sensor systems or types of sensors which may be utilized in various applications of the present invention include: total inorganic ion concentration sensors; total organic ion concentration sensors; ion selective sensors; optical sensors; conductivity sensors; etc. This list is not meant to be exhaustive, but rather exemplary of the various methods and techniques that may be utilized to detect either extraneous ion concentration, target ion concentration, or some other chemical or physical parameter useful in determining desired adjustments in operation of the primary and secondary electrode systems, to achieve a selected effect.

10. Applications When the Target Species is Not Charged

From the above descriptions, applications of methods according to present invention in systems wherein electrotransport is conducted, but the target species is not charged, will be understood. For example, electroosmosis may involve utilization of an electrotransport device in order to transport a charge species, to facilitate transfer of an uncharged target or therapeutic species. Such systems may involve applications of the general principles described above, however, the species being transported for therapy is not itself charged. Nevertheless, controlled environment processes may be desirable, and thus a primary electrode system and secondary electrode system operated generally as described above may be utilized. More specifically, the secondary electrode system may be utilized to control extraneous ion presence (or the presence of the ion being transported in order to facilitate transfer of the therapeutic species), to maintain constant pH or conductance, or to in some other manner desirably effect the active electrode reservoir.

11. Applications to Render Species Inactive, for Disposal

In some systems, the active or target species may be a controlled and dangerous substance, such as a narcotic. Disposal of the reservoir, after use, may be a problem for such systems. However, if the reservoir contains two selectively operable electrode systems therein, a selected current or potential can be applied between them which is sufficient to degrade or otherwise render the drug inactive, at termination of the delivery process.

More general principles in detail concerning application and methods according to the present invention will be understood from the following apparatus descriptions.

C. General Apparatus Usable and Applications of the Present Invention

1. General Electrode Construction

Figure 2:
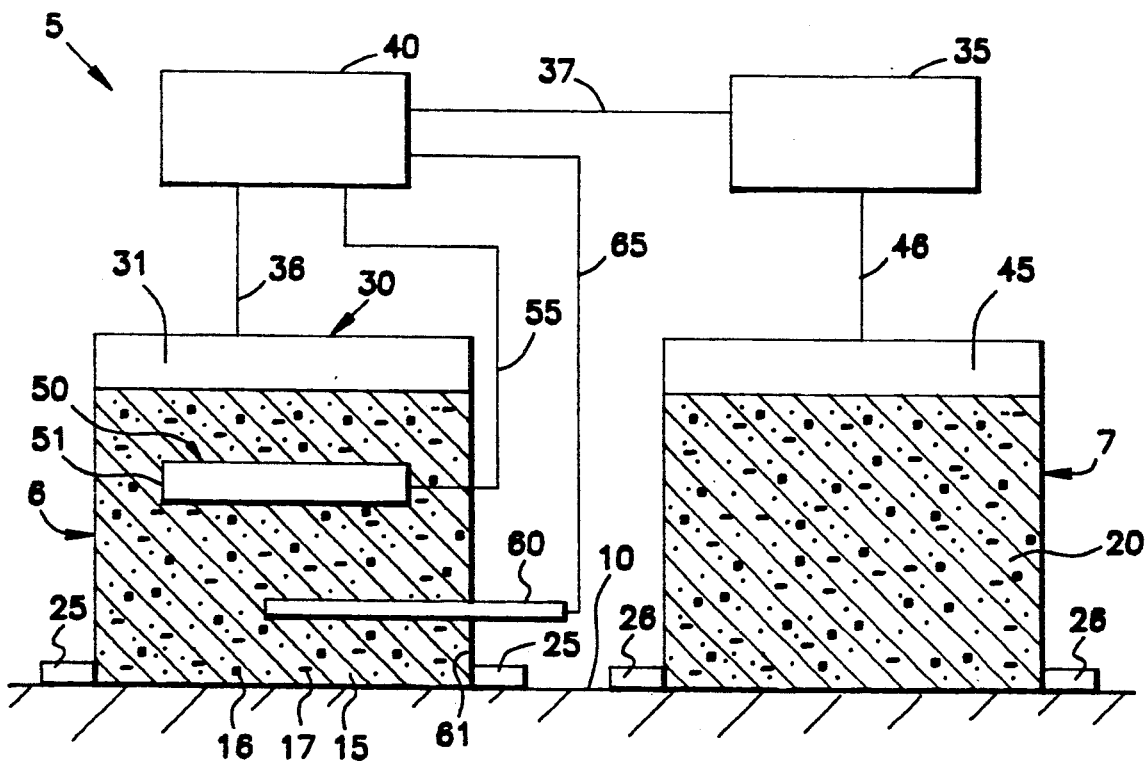
FIG. 2 is a schematic representation generally indicating apparatus usable according to the invention.

In FIG. 2, schematic representation is presented of an arrangement utilizable to effect methods generally described above, according to the present invention. In FIG. 2 an overall electrotransport drug delivery system 5 is depicted. This system 5 includes an active electrode reservoir 6 and an inactive electrode reservoir 7, both provided in electrical contact with a skin surface 10 of a subject to be treated. In general, active electrode reservoir 6 includes therein an electrolyte pool in the form of a gel or gel matrix 15 containing ionic drug species 16 to be delivered, as well as extraneous ions 17. The inactive or ground electrode reservoir 7 includes therein a gel or gel matrix 20 including sufficient electrolytes therein for passage of current therethrough, for example saline solution.

Both reservoirs 6 and 7 are provided in electrical communication with surface 10, retention being preferably achieved by means of skin-compatible pressure sensitive biomedical adhesive layers 25 and 26 respectively. In some instances a conductive adhesive provided directly between reservoirs 6 and 7, and skin surface 10 may be used.

A primary electrode system for arrangement 5 is illustrated generally at 30. The primary electrode system 30 generally comprises a grid 31 of a selected electrode material in electrical communication with power source 35. In FIG. 2, this is illustrated by means of communication lines 36 and 37, with power from power source 35 passing through a control module 40, referred to in more detail below. The control module 40 includes means for adjusting and controlling the amount of current provided to grid 31.

In general, grid 31 is provided in intimate contact (i.e. electrical or electrically conductive contact) with gel matrix 15, so that as current is applied to the grid 31, electromotive force is applied to ions, for example the drug species 16, (if charged) and the extraneous ions 17, supported in the matrix 15, driving same into the skin surface 10.

Still referring to FIG. 2, a companion electrode 45 to the primary electrode 31 is provided in the inactive or remote electrode reservoir 7. Electrode 45 provides for completion of the electrical circuit upon passage of current through the skin 10. Electrode 45 is in communication with power source 35 by means of communication line 46.

As thus far described, arrangement 5 may be a conventional iontophoresis electrode system: with either of electrodes 30 or 45 being an anode and the other being a cathode; with power source 35 being an appropriate source of current; and, with control arrangement 40 providing for current level control through the system. Arrangement 5, however, differs from conventional arrangements by means now described.

Still referring to FIG. 2, active electrode reservoir 6 of arrangement 5 includes therein a secondary electrode system 50. Electrode system 50 is different from system 30, i.e. when operated its effect on the ion content of reservoir 6 is different from the effect of electrode system 30. The specific effect selected will depend upon the specific effect needed, in application of the general methods described above. Electrode system 50 includes an electrode 51 in intimate (i.e. electrically conductive) contact with reservoir material 15. Current to or from electrode system 50 is provided by means of communication wire 55, from control unit 40.

As described thus far, control unit 40 can be utilized to control overall current between active electrode reservoir 6 and inactive electrode reservoir 7, i.e., current passing through the skin 10 of subjects being treated. Further, control unit 40 can be utilized to selectively control current through either and both of primary electrode arrangement 30 and secondary electrode arrangement 50, as well as the ground or inactive electrode 45. Appropriate circuitry means for control unit 40 to accomplish this may be through conventional circuitry means using principles within the knowledge of persons in the art of designing control circuits for current flow.

As previously indicated, control unit 40 may include microprocessor means to control relative current passing through primary electrode arrangement 30 and secondary electrode arrangement 50 pursuant to a preprogrammed schedule, and/or it may include means for adjustment of current through either or both of primary electrode arrangement 30 and secondary electrode arrangement 50, in response to feedback provided by a sensor arrangement within active electrode reservoir 6. Referring to arrangement 5 of FIG. 2, sensor arrangement 60 is shown located within reservoir 6, preferably immersed within gel 15 near an end region 61 of gel 15 located adjacent the skin surface 10. That is, in general the most important region of the entire reservoir 6 in which to determine ion presence is the region in the immediate vicinity of the skin surface 10, and it will in general be preferred to position the sensor arrangement 60 for detecting ion presence in that location.

The sensor 60 may be in a variety of arrangements, depending on the particular system utilized. For example, it may be a pH sensor or an ion selective electrode, as needed. Sensor 60 is shown in communication with control means 40 by communication arrangement 65, i.e., a wire arrangement or the like. It will be understood that for a system utilizing sensor 60, control means 40 may be provided with appropriate circuitry and processing arrangements so that in response to measurements taken by sensor 60 current through electrode arrangement 30 and electrode arrangement 50 could be adjusted to achieve a desired modification in the extraneous ion content of active electrode reservoir 6.

In general, the schematic of FIG. 2 will be appropriate: regardless of whether or not the primary electrode arrangement 30 is operated as an anode or a cathode; regardless of whether or not the secondary electrode arrangement 50 is operated in the same manner as the primary electrode arrangement; and, regardless of whether more current is carried by the primary electrode arrangement than the secondary electrode arrangement, or vice versa. Further, the schematic is not intended to indicate the relative locations of the primary electrode arrangement 30 and the second electrode arrangement 50 in all preferred embodiments. As explained previously with respect to this, what is generally required is: that the two not be in direct contact with one another so that current can pass directly therebetween without passage through the gel or gel matrix 15; and, that both be provided in intimate (i.e. electrically conductive) contact with the electrolytic gel or gel matrix 15.

Figure 3:
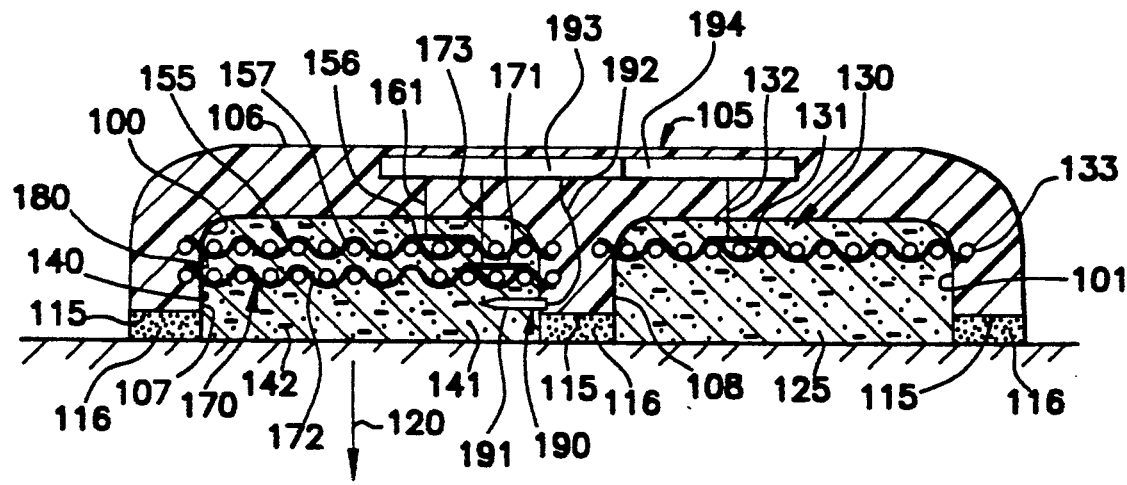
FIG. 3 is a cross-sectional view of a particular preferred apparatus usable according to the present invention, shown operationally positioned against a skin surface of a subject.

A schematic arrangement generally representing a typical electrode arrangement is also depicted in FIG. 3. The arrangement of FIG. 3, it will be understood, is generally according to the principles of the schematic of FIG. 2. Referring to FIG. 3, schematically depicted in cross section are two generally circular electrode-containing sections 100, 101 mounted within an electrotransport drug device 105. Device 105 includes an outer shell or housing 106 defining first and second cavities 107, 108. Preferably, housing 106 is formed from a flexible-, non-conductive material that can be comfortably and conveniently applied to an iontophoresis subject. Preferred material is a self-supporting medical-grade polyethylene foam, such as those available for 3M Corporation, Medical Products Division. For the arrangement shown, cavity 107 defines and retains therein the active electrode and active electrode reservoir, and cavity 108 defines and retains therein the companion "indifferent" or ground electrode and ground or inactive electrode reservoir.

In a typical preferred application, perimeter surfaces 115 of housing 106 include thereon a skin-compatible pressure-sensitive biomedical adhesive 116, (preferably non-conductive) intended to hold the electrode structure 105 in place on a subject's skin during iontophoretic drug delivery. Alternatively, the iontophoresis device may be held in place by other means, for example, a strap or tape, in which instance adhesive fields such as adhesive fields 116 may not be needed. As previously suggested, conductive skin adhesive can be used between the reservoirs and the skin. In general, delivery from arrangement 105 is downwardly into the skin, generally along the direction indicated by arrow 120 from cavity 107.

Referring still to FIG. 3, cavity 108 includes therein an electrolyte medium, typically electrically conductive gel or gel electrolyte solution 125, appropriate for carrying current from the skin surface to an electrode contained therein. In the arrangement shown in FIG. 3, an inactive or ground electrode arrangement 130 is depicted comprising a connector 131 attached to a wire 132. The connector 132 is shown in electrical communication with a grid 133 for dispersion of current (or current pickup) throughout a horizontal cross-section of chamber 108 for efficiency. The grid 133 should be well immersed within matrix 125 to ensure good electrical conductivity. A wide variety of materials may be utilized as a gel or gel matrix (in either reservoir), including agar, polyvinylpyrrolidone gels and those matrices described in U.S. Pat. No. 4,820,263, incorporated herein by reference. The gel or gel matrix may be a composite (layered) system.

Attention is now directed to chamber 107, which defines and contains therein the active electrode reservoir 140. Active electrode reservoir 140 includes therein gel matrix 141, which includes therapeutic agents 142 for delivery along path 120 into the skin of a subject. The gel matrix 141 may be generally as described for gel matrix 125, except of course it is at least loaded with the target ionic species, or precursor for the target species, to be delivered into the patient. The primary electrode reservoir 140 includes immersed therein the primary electrode arrangement 155 comprising electrically conductive contact 156 and dispersion grid 157. Electrical contact from a control unit and a power source to contact 155 is provided by means of wire 161.

Thus far, the arrangement described may be generally according to conventional iontophoretic drug delivery systems, such as the one described in U.S. Pat. No. 4,747,819 to Phipps et al., incorporated herein by reference.

A major difference between the arrangement of FIG. 3 and those of conventional systems is that active electrode reservoir 140 also includes therein a secondary electrode arrangement 170. Secondary electrode arrangement 170 comprises a contact 171 in communication with a dispersion grid 172. Electrical communication from a power source and/or control unit or the like to contact 171 is provided by means of wire 173.

Direct electrical contact (i.e., touching contact) between electrode arrangement 155 and secondary electrode arrangement 170 is avoided by means of non-conductive section 180 therebetween. In FIG. 3, each grid 157 and 172 is imbedded in the foam of the construction, so they are maintained spaced apart by a non-conductive portion 180 of that construction. Due to the porous nature of grids 157 and 172, it will be understood that both are in intimate contact with gel matrix 142, and thus both can influence the chemical content thereof and migration of species therethrough.

The arrangement of FIG. 3 also includes therein a sensor arrangement 190 for detecting or sensing the nature or change in nature of the gel matrix 142 during electrotransport. Sensor arrangement 190 includes a sensor 191, which is inserted within gel matrix 142, and a communication arrangement 192 (for example a wire circuit) for communication with control means or the like. Preferably, sensor 191 is oriented in a portion of gel matrix 142 substantially adjacent the skin surface of a patient being treated, i.e., sensor 191 is oriented just within cavity 107 from peripheral surface 115. Advantages derived from this are discussed above.

Figure 4:
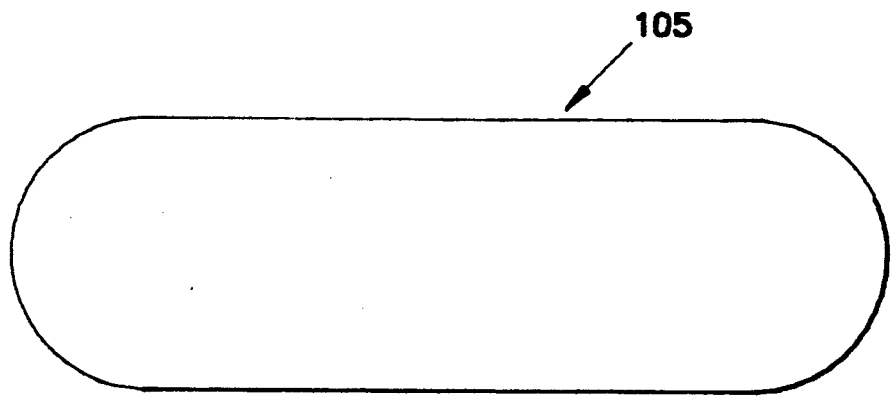
FIG. 4 is a top plan view of the arrangement shown in FIG. 3.

Control means and power source for complete operation of the arrangement of FIG. 3 are generally shown at 193 and 194 respectively. For the arrangement of FIG. 3 the control means 193 and power source 194 are imbedded within construction 115. In some applications they may be remote therefrom. In FIG. 4, a top plan view of the arrangement 105 illustrated in FIG. 3 is shown.

2. The Construction of the Primary Electrode

As previously explained, the primary electrode arrangement may be constructed for operation as either a cathode or an anode, depending upon the particular application of the principles of the present invention. In general, again depending upon the particular application, it may be constructed for operation as: an "inert" or "electrolysis" electrode; a sacrificial electrode; a plating electrode; and/or, an intercalation-type (or insertion-type) electrode. Herein, in this context, the phrase "inert" or "electrolysis" electrode, and variants thereof, is meant to refer to an electrode which does not itself participate in chemical change in the electrolyte solution during operation, but is used as an electrode during operation to generate either hydronium or hydroxide ions in the solution via typical electrolysis processes. Examples of such electrodes are platinum and carbon electrodes. The term "inert" electrode also includes an electrode which causes oxidation/reduction reactions, without plating, intercalation, insertion or sacrifice, to effect the electrolyte content of the reservoir. Herein, the term "sacrificial" electrode is used to refer to an electrode which is operated to release ions into the associated electrode reservoir during operation at the sacrifice (i.e., non-replaceable expense) of the electrode, for example, a wide variety of metal electrodes operated as anodes would be sacrificial electrodes, typical examples being silver, zinc and copper electrodes. The term "plating" electrode in this context is used to refer to an electrode which is operated to plate ionic species in solution at a surface thereof. An example of such an electrode would be a copper electrode operated as the cathode in a solution containing copper ions. During such operation copper ions will be reduced, plating copper onto the electrode. The terms "intercalation" and "insertion" electrode in this context is generally used to refer to arrangement providing for expulsion or incorporation of ionic species from or into the electrode upon oxidation or reduction of that electrode. An example of such an electrode is the sodium tungstate electrode described in the Phipps U.S. Pat. Nos. 4,747,819 and 4,744,787, supra. Other examples of such electrodes are the iridium oxide electrodes of U.S. Pat. Nos. 4,679,572 and 4,717,581; and, Robblee, L. S. et al., *J. Electrochem. Soc.*, Vol. 130, No. 3 p. 731–733 (1983); Pickup, P. G. et. al., *J. Electroanal. Chem.*, Vol. 220 p. 83–108 (1987); and, Dautremont-Smith, W. C.; Displays, p. 67–80 (April 1982); all of which incorporated herein by reference. The particular, specific, nature of the primary electrode will be dependent upon the particular transport to be conducted.

The primary electrode arrangement may comprise a single electrode or plurality of electrodes. It may comprise a porous grid or have a different structure. In general what is required, as indicated above, is an effective dispersive electrical contact with the gel matrix.

3. The Secondary Electrode

The secondary electrode may be constructed in any of a variety of manners, and may include any of the types of electrodes described above for the primary electrode arrangement. The secondary electrode should be selected to obtain selected changes in ionic species concentrations in the active electrode reservoir. Such changes or modifications would not be accomplished if the secondary electrode arrangement were constructed and operated identically to the primary electrode arrangement. The particular, specific, nature of the secondary electrode arrangement to be used in any given system will be dependent upon the effect on ion presence in the reservoir to be achieved, in accordance with the principles described herein.

4. The Remote Electrode Arrangement

The remote or companion electrode arrangement may be constructed of any of a variety of appropriate means utilized in electrotransport systems. The electrode arrangement may comprise, for example, electrodes as described above for the primary electrode arrangement and/or the secondary electrode arrangement. It will in general, of course, be operated in a manner opposite to that of the net manner of the primary and secondary electrode arrangements. That is, the companion electrode is selected to obtain the desired current flow through the subject, during electrotransport.

It will be understood that there is no basic principle requiring that the remote electrode not be involved in a drug delivery. That is, drug or therapeutic ion delivery from the remote electrode reservoir may be conducted simultaneously with the drug and/or selective ion delivery from the primary electrode reservoir arrangement, if desired. Thus, the present invention includes within its scope an arrangement which involves drug delivery from both reservoirs and appropriate secondary electrode arrangements within each of the reservoirs for control of ionic species concentrations therein.

5. Some Examples of Constructions and Methods According to the Present Invention The general principles of the present invention will be further understood from the following examples. The examples are intended to indicate how the basic principles may be applied, and various constructions that may be used for their application. It will be apparent from the examples that a wide variety of systems could be developed for specific control of therapeutic ion delivery.

a. Use of the Secondary Electrode to Control pH in the Active Electrode Reservoir An example of the use of the present invention to control pH (i.e., hydronium ion content) is as follows. Iridium oxide is an electrochromic material which can be reversibly oxidized and reduced. Oxidation of Ir(III) to Ir(IV) causes a hydronium ion to be released according to the reaction:

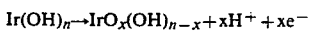

$$Ir(OH)_n \rightarrow IrO_x(OH)_{n-x} + xH^+ + xe^-$$

This oxidation reaction occurs at about 0.7 volts (versus Ag/AgCl).

Figure 5:
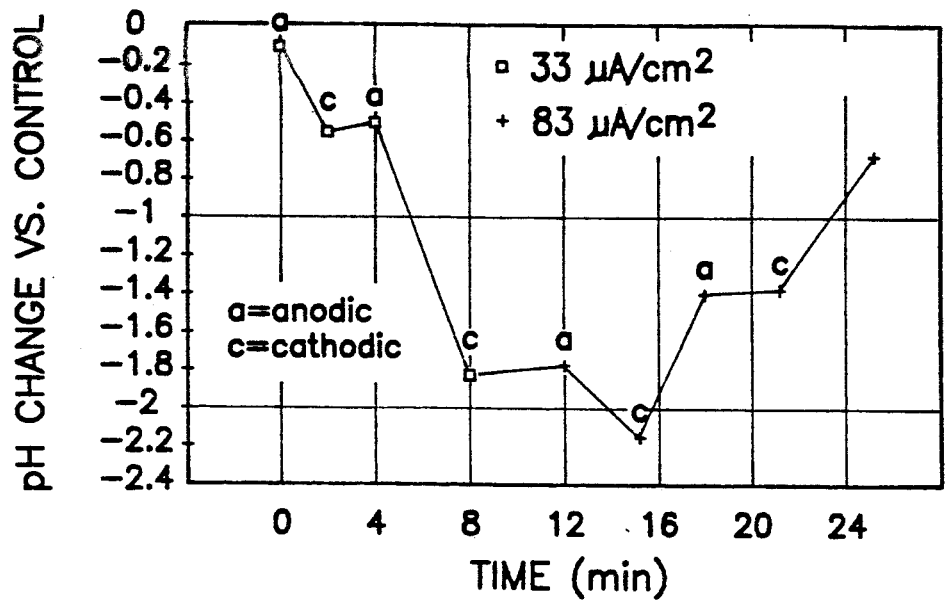
FIG. 5 is a graph representing pH changes with electrode operation, as described herein for an iridium oxide electrode.

FIG. 5 shows experimental results for the use of an iridium oxide coated wire to change the pH of 1 ml of a 0.05 molar (M)NaCl aqueous solution. As illustrated in the figure, the hydronium ion content of the solution was altered by two orders of magnitude by application of current of 10 to 25 microamps for several minutes. The figure also indicates that the pH can be decreased by application of an oxidative potential and increased by use of a reductive potential.

In pharmaceutical preparations, the hydronium ion content can often be critical in determining the stability, charge and biocompatibility of the preparation. A common method previously used for fixing the pH at a desired level has been through the use of buffering agents (for example, citrate and/or phosphate salts). The use of such buffering agents in pharmaceutical preparations for iontophoretic drug delivery systems can cause reduced efficiency of drug delivery, due to the introduction of non-drug ions (i.e., extraneous ions). For example, the use of a sodium phosphate buffer in the active electrode reservoir for the iontophoretic delivery of hydromorphone (delivered from an anode reservoir as a cation) would result in delivery of both hydromorphone cation and sodium ion. A sodium ion is much more mobile than a hydronium ion, so two problems would result: inefficient utilization of the power source (battery) of the device, since much of the current will be handled by transport of sodium ions instead of hydromorphone ions; and, inability to maintain a constant delivery rate of hydromorphone ion, for the reasons stated hereinabove. Similar inefficiencies would result from codelivery of phosphate (or citrate) anion with a drug ion delivered as an anion (for example, salicylate) during iontophoresis.

According to the present invention, then, a secondary electrode operable to oxidize Ir(III) to Ir(IV) [or reversibly operable to reduce Ir(IV) to Ir(III)] can be used to selectively adjust pH in the system as desired. Thus, pH can be made stable without additional buffering agents. That is, a drift in pH during operation of the primary electrode could be compensated by oxidation or reduction of the iridium oxide of the secondary electrode.

Continual and constant adjustment, via feedback, could be accomplished by providing a pH sensor in the system in communication with control means for the iridium oxide electrode. It will be understood that this application of the methods of the present invention is to maintain constant pH, and not to maintain a constant molar ratio for the target species. In fact, in this application the molar ratio for the target species will tend to decrease in time, if the only extraneous ions are the hydronium/hydroxyl ions.

Constant current for the system could be maintained through appropriate electronic circuitry means to maintain a balance of current among all of the electrodes in the system. Thus, for example, if the iridium oxide electrode was being used as an anode in the system wherein the primary electrode arrangement was also used as an anode, as the current to the secondary electrode arrangement is increased the current to the primary electrode arrangement could be simultaneously decreased to maintain a constant total of current in the system.

As with an iontophoretic device which delivers a therapeutic ion, control of reservoir pH is important for an electro-osmotic (electrotransport) device where an uncharged (neutral) therapeutic agent is delivered into the target tissue due to an applied electromotive force. For example, consider an anode reservoir contain a neutral polypeptide therapeutic agent suspended or dissolved therein and also containing cations such as $Na^+$ (added as the salt, e.g. NaCl). When the primary electrode, for example silver, is operated as an anode (to form AgCl), migration of $Na^+$ due to the applied electromotive force will result in loss of solvent (water) from the reservoir and the polypeptide dissolved therein. Loss of solvent from the reservoir can also result in loss of other agents present in the reservoir such as buffering agents. Polypeptide stability, in general, is dependent on the pH of the reservoir; and, therefore, loss of buffering capacity could result in a detrimental change in reservoir pH with time leading to polypeptide degradation. To counteract loss of buffering agent from the reservoir, the secondary electrode (e.g. iridium oxide) would be operated so as to create or remove $H^+/OH^-$ ion and maintain a preferred reservoir pH in a manner analogous to the iontophoretic device discussed above.

This principle can, of course, be extended to include the replacement or removal of any ion in the active reservoir of an electro-osmotic device by operation of a suitable secondary electrode. For example, in the preceding discussion of electro-osmotic polypeptide delivery, loss of $Na^+$ can be maintained at a preferred concentration within the reservoir by oxidation of a secondary electrode composed of sodium tungstate as discussed in Section 5d to follow.

b. Use of the Secondary Electrode to Convert Drug Base or Drug Acid to Drug Ion in the Electrode Reservoir Many drug moieties are available in "free base" or "free acid" form. Such drugs are sparingly soluble in water, and are sometimes more stable than the salt form (ionic form) of the drug. The principles described in this section provide practical means for iontophoretic delivery of the drug "free base" or "free acid". Use of a hydronium ion generating/absorbing secondary electrode (for example an iridium oxide electrode) can be used to create in situ the charged form of the drug, which can then be iontophoretically delivered.

For example, if the anode reservoir contains the drug-base hydromorphone (alkaloid) suspended in a hydrogel at pH 8, than approximately one-half of the alkaloid will be uncharged. Oxidation of a secondary electrode composed of a iridium oxide (coated on a conductive substrate material) would generate hydronium ion via the reaction presented in the immediate proceeding section.

The current and duration of the operation of the iridium oxide secondary electrode would depend on the amount of hydromorphone alkaloid present in the reservoir. Preferably, only a stoichiometric amount of $H^+$ would be generated by the secondary electrode, so as to convert essentially all of the alkaloid to ionic hydromorphone, thus avoiding the generation of excess $H^+$. The current/time profile for operation of the secondary electrode could be preprogrammed or could be controlled by a pH sensor present in the reservoir. The particular rate of generation of $H^+$ by the secondary electrode would preferably be no greater than the rate of conversion of alkaloid to hydromorphone cation. This would insure that a hydronium ion does not substantially compete with hydromorphone cation for transport, as would be the case of $H^+$ were generated at too large of a rate, even though only generated in a stoichiometric amount in total.

The primary electrode for this example could be any of the previously discussed arrangements, but would preferably be selected so as to generate little or no $H^+$ or $OH^-$ ion. In other words, conversion of the alkaloid to the cation would primarily be controlled by operation to the secondary electrode.

If only a primary electrode system capable of generating $H^+$ ion were used, its operation would result in either too great a rate of $H^+$ generation, or too great a total of $H^+$ generation (i.e. greater than stoichiometric) in order to achieve a desired rate of transport. This would lead to pH instability and loss of efficient delivery of a hydromorphone ion.

Use of an excessive amount of hydromorphone alkaloid in the reservoir may in some instances prevent a pH instability, but it would result in waste of hydromorphone and create a concern for safe disposal of the iontophoretic system after use.

Alternatively, the hydromorphone alkaloid could be converted to the cationic form by removal of $OH^-$ in the reservoir, upon operation of the secondary electrode. Removal of $OH^-$ in a water-containing reservoir results in a lowering of the pH of the reservoir, and thus a conversion of the alkaloid to the cationic form.

In the case where the drug to be delivered is available or can be produced in the acid form (uncharged) then the secondary electrode system would be used to generate hydroxyl ion or remove hydronium ion. For example, salicylic acid is a sparingly soluble drug. Delivery of salicylate could be a accomplished by the placement of the acid form in the cathode reservoir of an iontophoretic device, with a follow-up step of conversion to salicylate anion by generation of $OH^-$ via reduction of water at a glassy carbon secondary electrode, or by removal of $H^+$ from the cathode reservoir by reduction of an iridium oxide secondary electrode.

For such a system, the primary electrode, which could be a plating or sacrificial electrode, but preferably not substantially $H^+$ or $OH^-$ generating/removing, would supply additional electromotive force such that the total force (primary+secondary) would drive the salicylate anion into the skin at an appropriate rate.

The limitations on the rate and duration of $OH^-/H^+$ generation/removal (i.e. current) by the secondary electrode would be similar to those discussed above in the hydromorphone alkaloid example.

The use of the secondary electrode, as opposed to the primary electrode, to generate or remove hydronium or hydroxyl ion is advantageous in that a stoichiometric amount of $H^+$ or $OH^-$ ion needed to convert free base or free acid drug to the ionic form can be efficiently generated. That is, the primary electrode arrangement can be selected to generate appropriate electromotive force for ion transport without simultaneous generation of hydronium or hydroxyl ion. This would generally avoid the production of excess $H^+$ or $OH^-$ in the system, facilitating patient comfort and good control over pH and ion delivery.

c. Use of the Secondary Electrode to Create a Mixture of Charged and Uncharged Drug for Control of Total Drug Delivery (passive and active)

In general, uncharged organic species penetrate the skin more readily than charged organic species when little or no electromotive force is applied to the reservoir. This is known as "passive" or "diffusive" drug delivery. This observation leads to a preferred drug delivery system where the ratio of charged to uncharged drug (e.g. hydromorphone or salicylate) can be altered so that delivery is: mostly or wholly due to diffusion of uncharged drug; or, mostly or wholly due to electrotransport of charged (ionic) drug; or, to a combination of diffusion and electrotransport. A preferred combination of delivery by diffusion and electrotransport via creation of a preferred charged to uncharged drug ratio in the reservoir can be accomplished through maintenance of a particular pH upon use of a secondary electrode system as described above. This can lead to a optimized energy efficient delivery system.

For example, if hydromorphone is required by a patient at a low dose rate for most of the day to control pain, but at a much higher dose rate during part of the day, then the preferred delivery system discussed above could be operated in a mostly diffusive mode (i.e. at a reservoir pH where most of the drug is uncharged) when the low dose rate is required and in an electromotive mode (i.e. at a pH where some or all of the drug is cationic and the primary electrode supplies electromotive force) when the higher dose rate is required.

In general terms, this preferred drug delivery system can alter the type and size of the force applied to the drug species by adjusting the pH of the reservoir and the electric potential (voltage) supplied by the primary electrode. The type of force can be shifted from mostly chemical in nature (i.e. resulting from a chemical potential gradient) to mostly electromotive in nature (i.e. resulting from an electrical potential gradient). Optimal energy efficiency is achieved by matching the therapeutic dose needed by the patient to the least energy consuming combination of diffusive and electromotive force needed to meet the dose requirement. Generally, the least energy consuming combination would be that which is as diffusive in nature as possible.

In a special instance wherein the uncharged drug diffuses through the tissue (skin) at a rate sufficient to meet the highest dose requirement of the patient, but where a lower dose rate is required by the patient periodically through the day, then the pH at the reservoir could be altered by the secondary electrode to increase the fraction of charged drug in the reservoir and thus lower drug delivery.

In this latter instance, primary and secondary electrode systems are needed in the active electrode reservoir but no remote or ground electrode is required, since only a diffusive process is required to deliver a sufficient (therapeutic) quantity of the drug. Thus, the latter example is not an electrotransport, but rather is an application of principles described herein to facilitate a diffusive process, by providing an electrode system within the reservoir for drug delivery. The electrode system would generally include first and second operable electrode arrangements, selected for control of pH. A sensor system, pre-programed system or both could be used for control.

This principle of use of two electrodes in the active or delivery reservoir to alter reservoir conditions and thus change permeability of therapeutic agent can be extended to include chemical or electrochemical alteration. For example, conversion of a drug precursor in the reservoir to an active and/or more permeable form. This conversion can be conducted before placement of the reservoir against the skin, or after. It may be conducted continuously or selectively. It will be understood that the technique may be applied if the drug has a polar and unpolar (or less polar) form, of different mobility, even if neither form is charged, provided the electrodes can be used to convert the drug between the two forms. Of course, if the drug has both charged and uncharged forms, the charged form will be the more polar.

d. Use of the Secondary Electrode to Control the Inorganic Ion Content of the Active Electrode Reservoir Inorganic ions such as $Na^+$, $K^+$, $Ca^{2+}$, $Cl^-$, $SO_4^{2-}$, $HCO_3^-$, and $PO_4^{3-}$ may be present in the active electrode reservoir, for example as additives to enhance some property of the reservoir (e.g., drug stability, pH stability, conductivity and/or biocompatability) or their presence may be inadvertent or unavoidable (e.g., impurities present in reservoir ingredients, pre-existing ions on the skin surface, taken-up during iontophoresis especially in a reverse polarity device as described by Lattin, G. A., U.S. Pat. No. 4,406,658). Changes in the concentration of inorganic ions in the active reservoir during electrotransport can result in changes in the delivery rate of the target ion as discussed previously, and as reported in Experiment 1 which follows. A secondary electrode which releases/generates or absorbs/removes inorganic ions upon oxidation or reduction can be used to control the inorganic content of the active reservoir in a manner analogous to the use of an iridium oxide electrode to control the pH, discussed previously. One class of electrodes which releases or removes $Na^+$, $K^+$, and $Ca^{2+}$ and other inorganic ions are inorganic intercalation or insertion materials. A specific example is sodium tungsten-bronze which releases $Na^+$ when oxidized and absorbs $Na^+$ when reduced, via the reversible reaction:

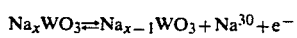

Other possible secondary electrode materials are graphite intercalation compounds, specifically:

$$nC + Na^+ + e^- \rightleftharpoons C_nNa$$

for release or removal of $Na^+$; or, $$C_nFeCl_2 + Cl^- \rightleftharpoons C_nFeCl_3 + e^-$$

for release or removal of $Cl^-$.

Another class of possible electrode materials are conductive polymers, for example, those described by Miller, L. L. et al in J. Am. Chem. Soc., Vol. 106, pages 6861-6863; J. Electroanal. Chem., Vol. 261, pages 147-164; J. Electroanal. Chem., Vol. 247, pages 173-184. The polymer electrodes can be polypyrrols, polyanilines, polythiophenes, and modifications thereof. In general, use of polymeric electrodes results in the release or absorption of anions and cations (organic or inorganic) to maintain charge neutrality locally within their structures. For example, a composite electrode composed of poly(N-methylpyrrolylium) and poly(styrenesulfonate) will cathodically absorb cations and anodically release cations. Anions can be anodically absorbed or cathodically released by oligomeric 3-methoxythiophene.

For example, consider as an anode reservoir of the electrode transport device a reservoir which contains the drug cation hydromorphone (as the HCl salt). Also, assume that the inorganic extraneous ion $Na^+$ is also present in the anode reservoir. During operation of this device, sodium ion will be depleted from the reservoir at a greater rate than is the hydromorphone, due to the relatively high mobility of $Na^+$ through skin as compared with hydromorphone. As shown in FIG. 1 and discussed in Experiment 1 below, the result will be an increase in the hydromorphone delivery rate with time, at constant current. To maintain a constant hydromorphone delivery rate with time, a secondary electrode which generates $Na^+$ at a rate necessary to maintain a constant molar fraction of the hydromorphone in the reservoir can be used.

e. Use of the Secondary and Primary Electrodes in the Active Reservoir to Convert Drug Therein to an Inactive Form In general, after termination of drug delivery from an electrotransport device, some drug will remain in the active reservoir. It may be desirable to "inactivate" or "degrade" or "convert" the drug to an inactive or nonextractable form to prevent inadvertent or intentional post-treatment use of the drug. This conversion of drug to an inactive form after device removal from the patient can be accomplished by use of the primary and secondary electrode by allowing one to act as the "counter" electrode for the other.

Either electrode (or both) can cause direct electrochemical degradation of the drug if the electrode potential is sufficiently large so that oxidation or reduction of the drug will occur (oxidation at the anode, reduction at the cathode). For example, electrochemical degradation of hydromorphone will occur at a platinum or glassy carbon electrode if the anodic potential exceeds 500 mV (versus Ag/AgCl).

The primary or secondary electrode material can be selected and operated so as to cause creation of a species which results directly or indirectly in the conversion of drug in the active reservoir to an inactive or nonextractable form. For example, the secondary electrode could be iridium oxide or platinum or another material which can generate hydronium or hydroxyl ion. Many drugs will rapidly degrade at high and/or low values of pH and therefore use of a secondary electrode to change the pH (as described previously) can result in conversion of the drug to an inactive form.

Alternatively, the primary or secondary electrode material can be selected so that its operation after device removal from the patient causes the release or generation of a chemical species which then reacts with, complexes with, or otherwise inactivates the drug, or converts the drug to a nonextractable form. For example, if the anode reservoir contains hydromorphone and the secondary electrode is silver, then operation of the secondary electrode as an anode after device removal will generate silver ion which will cause degradation of hydromorphone and additionally create a silver-rich active reservoir from which recovery of hydromorphone would require extensive processing. In this example, the silver secondary electrode may be dormant during electrotransport of drug from the device when on the patient and be activated when the device is removed from the body of the patient. When the device is removed, the control circuit would cause the primary electrode to serve as a cathode and the silver secondary electrode as an anode and as a result ionic current would flow between the secondary and primary electrodes (the remote electrode is not functional in this mode of operation). The primary electrode could also cause inactivation of the drug by a separate mechanism, for example, production of hydroxyl ion or electrochemical reduction of the drug (when operated as a cathode).

In general, the inactivation of drug in the active reservoir can be accomplished upon device removal if the active reservoir contains at least two electrodes so that an electrical potential can be applied between them such that one or both of the electrodes can inactivate the drug by the mechanisms discussed above (pH control, electrochemical degradation, chemical reaction, and/or reservoir contamination, e.g., with silver ion).

f. Experimental Examples

Experiment 1

The following experiment illustrates that, in the presence of highly mobile extraneous ions, direct delivery rate is shown to increase in time at constant current.

Aqueous solutions of hydromorphone (HM) and selected inorganic ions were prepared at total cation concentrations of 0.1 molar. The inorganic ions employed were sodium, potassium, calcium and magnesium, used as the chloride salts. The solutions were placed in the donor compartment of a two-chamber, flow-through glass cell modified to accommodate a silver anode and a silver chloride cathode. Dermatomed pig skin was placed between the donor and receptor compartments. The contact area between the donor solution and the skin was 8 cm². A 0.1 molar sodium chloride aqueous solution was pumped through the receptor compartment at 3 ml per hour. The experiment was performed in triplicate at a current of 1 milliamp (i.e., 125 microamps per cm²).

In Table 1 below, the results from four solutions are reported. The four solutions comprised one each of the four cations in solution with hydromorphone as hydromorphone hydrochloride. In Table 1, both the molar concentration and mole fraction, initial and final, are reported. By comparison of these figures, one observes that the concentrations of both the hydromorphone and the extraneous ion decreased during operation of the cell. Also, it is observed that the molar fraction of the more mobile extraneous ion was decreasing, while the molar fraction of the less mobile hydromorphone ion was increasing.

In FIG. 1, a plot of the rate of delivery of the hydromorphone (in micrograms per hour) at various time periods is illustrated. The graph shows a linear increase in the hydromorphone delivery rate observed as a function of time, for solutions initially containing approximately equal molar concentrations of $HM^+$ and inorganic ions.

TABLE 1

| Solution | Ion | Molar Concentration | | Mole Fraction | |
|---|---|---|---|---|---|
| | | Initial | Final | Initial | Final |
| 1 | Na | 0.047 | 0.029 | 0.435 | 0.357 |
| | HM | 0.061 | 0.053 | 0.565 | 0.643 |
| 2 | K | 0.049 | 0.021 | 0.497 | 0.312 |
| | HM | 0.049 | 0.046 | 0.503 | 0.688 |
| 3 | Mg | 0.048 | 0.038 | 0.481 | 0.445 |
| | HM | 0.051 | 0.048 | 0.519 | 0.555 |
| 4 | Ca | 0.049 | 0.039 | 0.490 | 0.437 |
| | HM | 0.051 | 0.050 | 0.510 | 0.563 |

Experiment 2

That the relationship between applied current and delivery of a target ion, for a system involving no extraneous ions, is linear is illustrated by the following example. The example is also reported in the literature at Phipps et al. "Transport of Ionic Species Through Skin," supra (1988). A two-compartment, vertical glass diffusion cell was used. A silver/silver chloride cathode was introduced into the receptor compartment by inserting the electrode wire into an inlet port. Excised rabbit, pig or human skin, approximately 8 cm$^2$ in area, was placed on a mesh which served as a support to the excised skin. The donor compartment, the excised skin and the receptor compartment were clamped together. One molar aqueous solution of the drug chloride was prepared and poured into the donor compartment. The cations used in the study were lithium, sodium, magnesium, potassium, calcium, salicylate, pyridostigmine and propranolol.

A silver anode was placed in the donor compartment which contained 7 ml of drug solution. A septum cap was placed on the donor compartment to minimize loss due to evaporation. The cathode and anode wires for each cell were connected to a nine-channel power source. Experiments with each type of skin were run in duplicated currents between 0 and 2 milliamps for 24 hours.

A flow-through diffusion cell system, which allowed for nine different experiments to be run simultaneously, was employed. An aqueous solution of 0.1M NaCl was supplied to a nine-channel peristaltic pump and pumped to the flow rate of 6 ml per hour into the receptor compartments of the nine diffusing cells. The water jacketed receptor compartment was maintained at 37° C. by a circulator bath, and the receptor fluid was stirred by placing the cells in the nine-cell magnetic drive console. Samples were continuously collected through the sampling outlet of the receptor compartment at two-hour intervals by nine-channel fraction collectors. The iontophoretic current for each cell was controlled by a constant current power source.

The drug content of the receptor compartment was determined by atomic absorption spectrophotometry (for inorganic ions) or by high-performance liquid chromatography (for organic ions).

Figure 6:
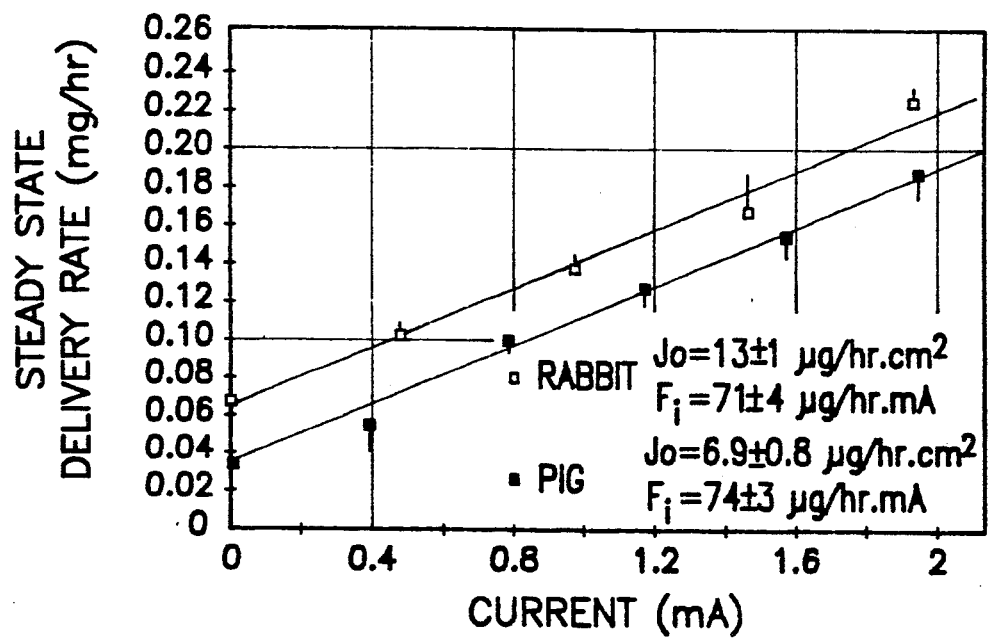
FIG. 6 is a graph representing linear dependence of ion delivery rate, for the experiment described in Experiment 2.

A linear dependance of the rate of drug delivery and current was observed for each of the ions studied. An example of this is indicated in FIG. 6, which shows a plot of lithium delivery rate as a function of the current for pig and rabbit skin. In general, the efficiency of drug delivery was found to decrease with increasing molecular weight and with increasing ionic charge.

Experiment 3

The independence of drug delivery rate on concentration of the drug species, above a threshold concentration and at constant current, is demonstrated by the following example. The example was also reported in Padmanabhan et al., "In Vitro and In Vivo Evaluation of Transdermal Iontophoretic Delivery of Hydromorphone," supra (1990). For the in vitro study, a two-compartment vertical glass diffusion cell was used. A silver chloride cathode was placed in the receptor compartment (4 ml capacity) and a silver mesh anode in the donor compartment. Excised pig skin was placed on a Delrin ® support fixture and clamped in place between the two compartments with the stratum corneum facing the donor compartment. The contact area between the donor solution and the excised skin was 8 cm$^2$. Pig skin was obtained from the mid-dorsal region of domestic, weanling pigs by dermatome at a thickness of about 600 microns. Skin samples were stored frozen prior to use.

The jacketed receptor compartment was maintained at a temperature of about 37° C. by a circulating water bath, and a 0.1M NaCl solution was pumped through the receptor chamber at a flow rate of about 3 and 6 ml per hour. The donor compartment was filled with 7 ml of hydromorphone hydrochloride (HMHCl) solution at selected concentrations from 0.01 molar (10 millimolar) to 0.8 molar (800 millimolar). The anode and cathode were connected to a constant current power supply accurate to within 5% of a set point value. Experiments were performed at currents of up to 2.0 milliamperes (mA) for 24 hours.

In a typical experiment, the HMHCl solution was placed in the donor compartment for 18 hours prior to the application of current. This was done to ensure that no leaks were present in the donor compartment prior to iontophoresis, and to allow for determination of the passive hydromorphone flux through each skin sample. After 18 hours, the donor compartment was emptied, rinsed and filled with fresh drug solution. A constant current was then applied for 24 hours, followed by 24 hours of passive delivery. In some experiments, the pre-iontophoretic passive phase and/or the post-iontophoretic passive phase were not performed.

During the 66-hour duration of the typical experiment, samples were collected continuously at two-hour intervals. The weight of each receptor sample was recorded, and the hydromorphone concentration of selected samples was determined by HPLC using UV detection at 280 nanometers. A 5 nanometer C18 column (Dupont Instruments, Wilmington, Del.) was used. The mobile phase was comprised of 59% 0.005M heptane sulfonic acid, 40% methanol and 1% acetic acid. The flow rate was set at 1 ml per minute.

Steady-state delivery rates were determined for each skin sample by multiplying the steady-state receptor concentration (achieved in approximately 10 hours) by the receptor flow rate, which was calculated from the weight of each two-hour receptor sample. Average steady-state rates for each skin sample were calculated for five consecutive values observed between 12 and 24 hours after application of the current.

In Table 2 below, a comparison of average steady-state delivery rates for pig skin from aqueous hydromorphone HCl solutions at different concentrations (where n = the number of skin samples) is presented. As can be seen, the average rate of delivery (microgram per hour) was relatively constant, regardless of the drug concentration.

TABLE 2

A comparison of the average steady-state delivery rates through pig skin from aqueous hydromorphone HCl solutions at different concentrations.

| Drug Concentration (millimolar) | n | Average Steady-State Rate ($\mu$g/hr) ± SD |
| --- | --- | --- |
| 10 | 3 | 1049 ± 183 |
| 30 | 3 | 1269 ± 43 |
| 100 | 19 | 1150 ± 159 |
| 400 | 3 | 1118 ± 180 |
| 800 | 3 | 1000 ± 71 |

It will be understood that experiments 1, 2 and 3 reported above generally provide the background observations described in Sections A1-A3 of the detailed description above, and which provide some of the basis for applications of the present invention to control extraneous ion concentrations in active electrode reservoirs.

What is claimed is:

1. A method of conducting electrotransport comprising the steps of:
   (a) selectively operating a primary electrode arrangement to provide electromotive force to transport ions from an active electrode reservoir; and,
   (b) selectively operating a secondary electrode arrangement such that the effect of the electrochemical reactions generated by the secondary electrode arrangement on the ionic content of the active electrode reservoir is different from that of the primary electrode arrangement, to selectively effect relative concentrations of ions in the active electrode reservoir.

2. A method according to claim 1 wherein:
   (a) said step of operating a primary electrode arrangement comprises operating the primary electrode arrangement as an anode; and,
   (b) said step of selectively operating a secondary electrode arrangement comprises selectively operating the secondary electrode arrangement as an anode.

3. A method according to claim 2 wherein:
   (a) said step of operating a primary electrode arrangement includes operation to transport at least one target cation species and at least one extraneous cation species from the active electrode reservoir; and,
   (b) said step of selectively operating a secondary electrode arrangement includes introducing at least one extraneous cation species into the active electrode reservoir.

4. A method according to claim 1 wherein:
   (a) said step of operating a secondary electrode arrangement is conducted to selectively maintain a concentration of a selected ion species in the active electrode reservoir at a constant level.

5. A method according to claim 4 wherein:
   (a) said step of operating a secondary electrode arrangement is conducted to selectively maintain pH in the active electrode reservoir substantially constant during said step of operating a primary electrode arrangement.

6. A method according to claim 1 wherein:
   (a) said step of operating a primary electrode arrangement includes operation to transport at least one target ion species and at least one extraneous ion species from the active electrode reservoir; and,
   (b) said step of selectively operating a secondary electrode arrangement includes introducing at least one extraneous ion into the active electrode reservoir; the extraneous ions introduced into the active electrode reservoir by the secondary electrode arrangement including at least one of the same species as transported therefrom by the primary electrode arrangement.

7. A method according to claim 1 wherein:
   (a) said step of continuously operating a primary electrode arrangement includes operation to transport at least one target ion species and at least one extraneous ion species from the active electrode reservoir; and,
   (b) said step of selectively operating a secondary electrode arrangement includes operation to remove at least one extraneous ion from the electrode reservoir by means other than transport.

8. A method according to claim 1 including a steps of:
   (a) modifying relative current flow through the primary electrode arrangement and the secondary electrode arrangement during said method; and,
   (b) selectively adjusting relative current flow through the primary electrode arrangement and the secondary electrode arrangement to maintain a constant current flow through a subject of the electrotransport.

9. A method according to claim 1 including the steps of:
   (a) providing a selected initial extraneous ion concentration in the active electrode reservoir at initiation of said step of operating the primary electrode arrangement; and,
   (b) conducting the operation of the secondary electrode arrangement in a manner constantly maintaining a concentration of extraneous ions within 30% of the initial extraneous ions concentration, throughout said step of operating the primary electrode arrangement.

10. A method according to claim 1 including a step of operating both of the primary electrode arrangement and the secondary electrode arrangement, by passage of current therethrough, simultaneously during at least a portion of said electrotransport.

* * * * *